(12) United States Patent
Harris et al.

(10) Patent No.: US 7,565,208 B2
(45) Date of Patent: Jul. 21, 2009

(54) CATHETER WITH SENSOR TIPS, TOOL AND DEVICE AND METHODS OF USE OF SAME

(75) Inventors: Chad G. Harris, Albertsville, MN (US); Matthew L. Hawk, Otsego, MN (US); Timothy J. Mickley, Elk River, MN (US); Dorin Panescu, San Jose, CA (US); Maria Palasis, Wellesley, MA (US); Jacob Rooney, Belgrade, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 717 days.

(21) Appl. No.: 11/037,342

(22) Filed: Jan. 19, 2005

(65) Prior Publication Data
US 2005/0215945 A1   Sep. 29, 2005

Related U.S. Application Data

(60) Provisional application No. 60/556,059, filed on Mar. 25, 2004.

(51) Int. Cl.
*A61N 1/02* (2006.01)

(52) U.S. Cl. .............................. 607/116; 607/2; 607/3; 606/41; 604/66

(58) Field of Classification Search ............. 604/22, 604/66, 514; 606/41; 607/1–3, 115, 116, 607/119, 122
See application file for complete search history.

(56) References Cited

U.S. PATENT DOCUMENTS

| 4,559,951 | A |   | 12/1985 | Dahl et al. | |
|---|---|---|---|---|---|
| 4,721,115 | A |   | 1/1988 | Owens et al. | |
| 5,971,983 | A | * | 10/1999 | Lesh ........................ | 606/41 |
| 6,165,164 | A |   | 12/2000 | Hill et al. | |
| 6,602,242 | B1 |   | 8/2003 | Fung et al. | |

FOREIGN PATENT DOCUMENTS

EP            1 125 548 A       8/2001

* cited by examiner

*Primary Examiner*—Carl H Layno
*Assistant Examiner*—Deborah Malamud
(74) *Attorney, Agent, or Firm*—Vidas, Arrett & Steinkraus

(57) ABSTRACT

An apparatus and method for catheter-based sensing and injection at a target site within a patient's body. An injection catheter is equipped with electrodes at its distal end which contact the surface of a target site, such as an AV node of the heart. Electrical signals detected at the target site by the electrodes are fed via leads to the proximal end of the catheter, where they are received by a monitor, such as an EKG monitor. If the electrical signals satisfy predetermined criteria, a needle within the catheter is extended into the target site, and a therapeutic agent is injected into the target site.

16 Claims, 14 Drawing Sheets

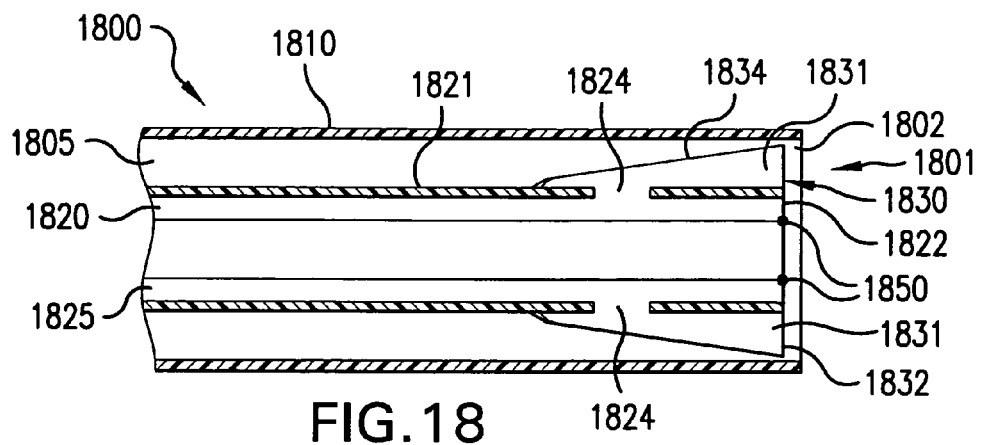
FIG. 18
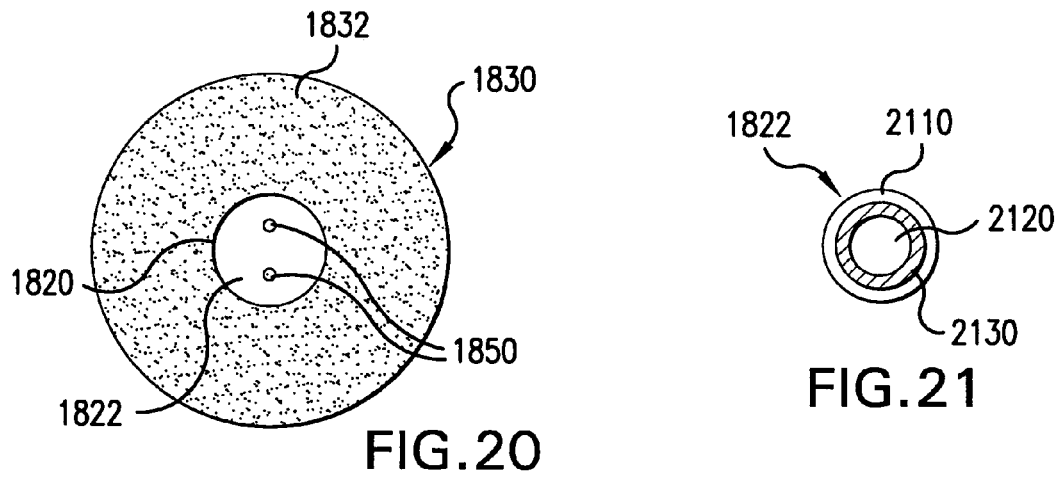
FIG. 20
FIG. 21
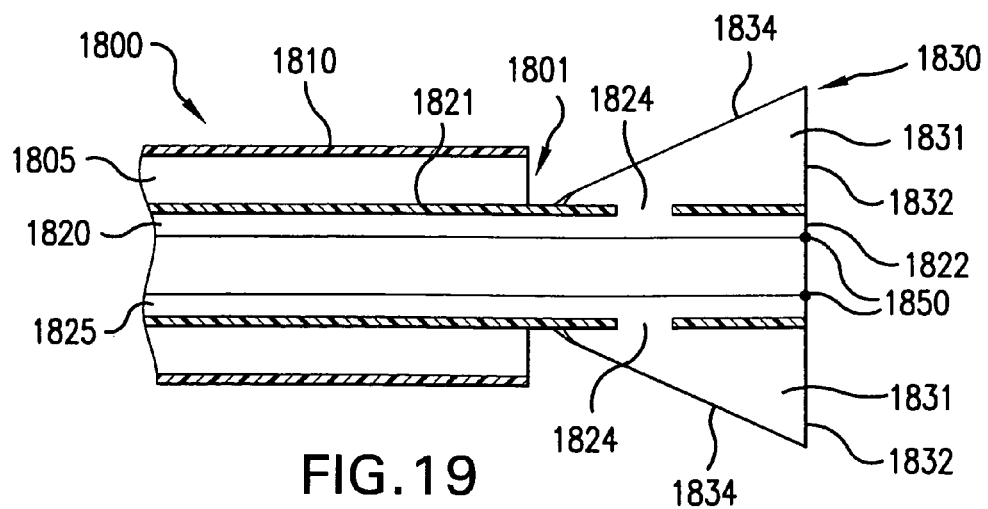
FIG. 19

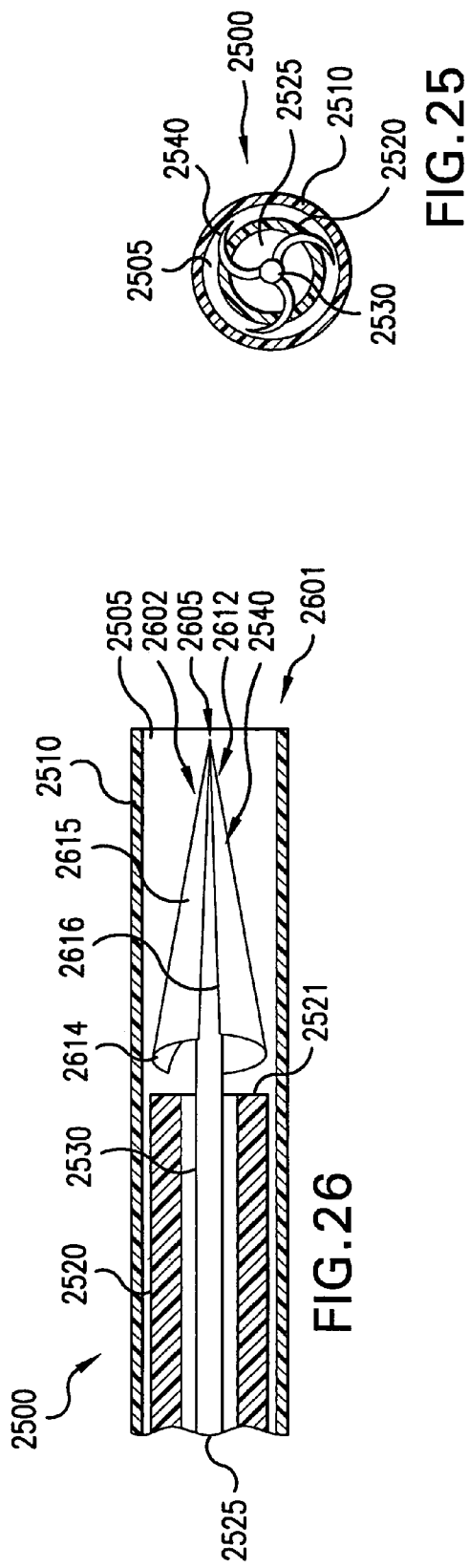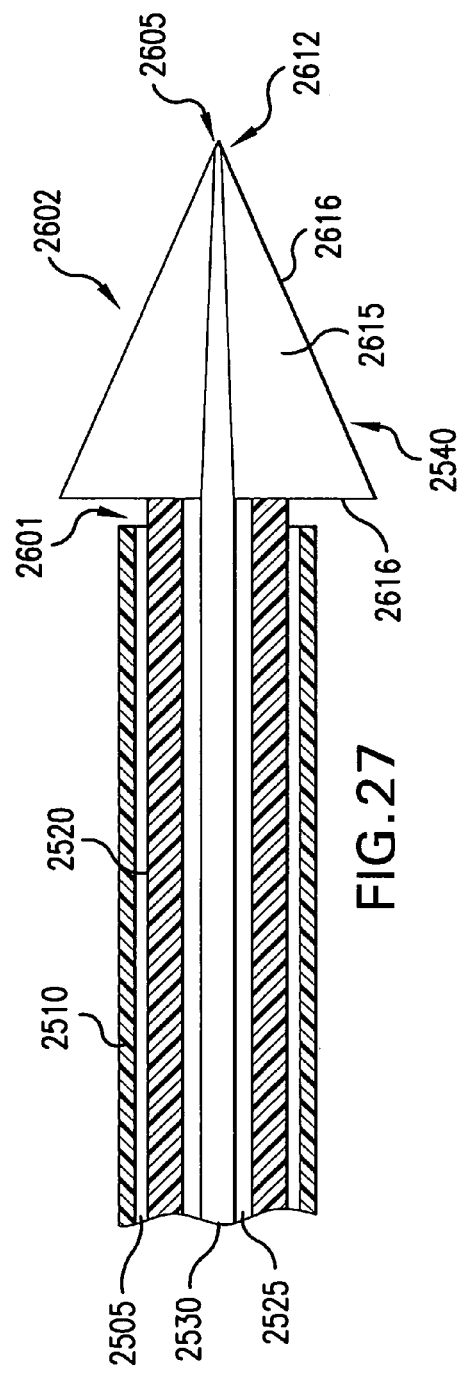
FIG.25
FIG.26
FIG.27

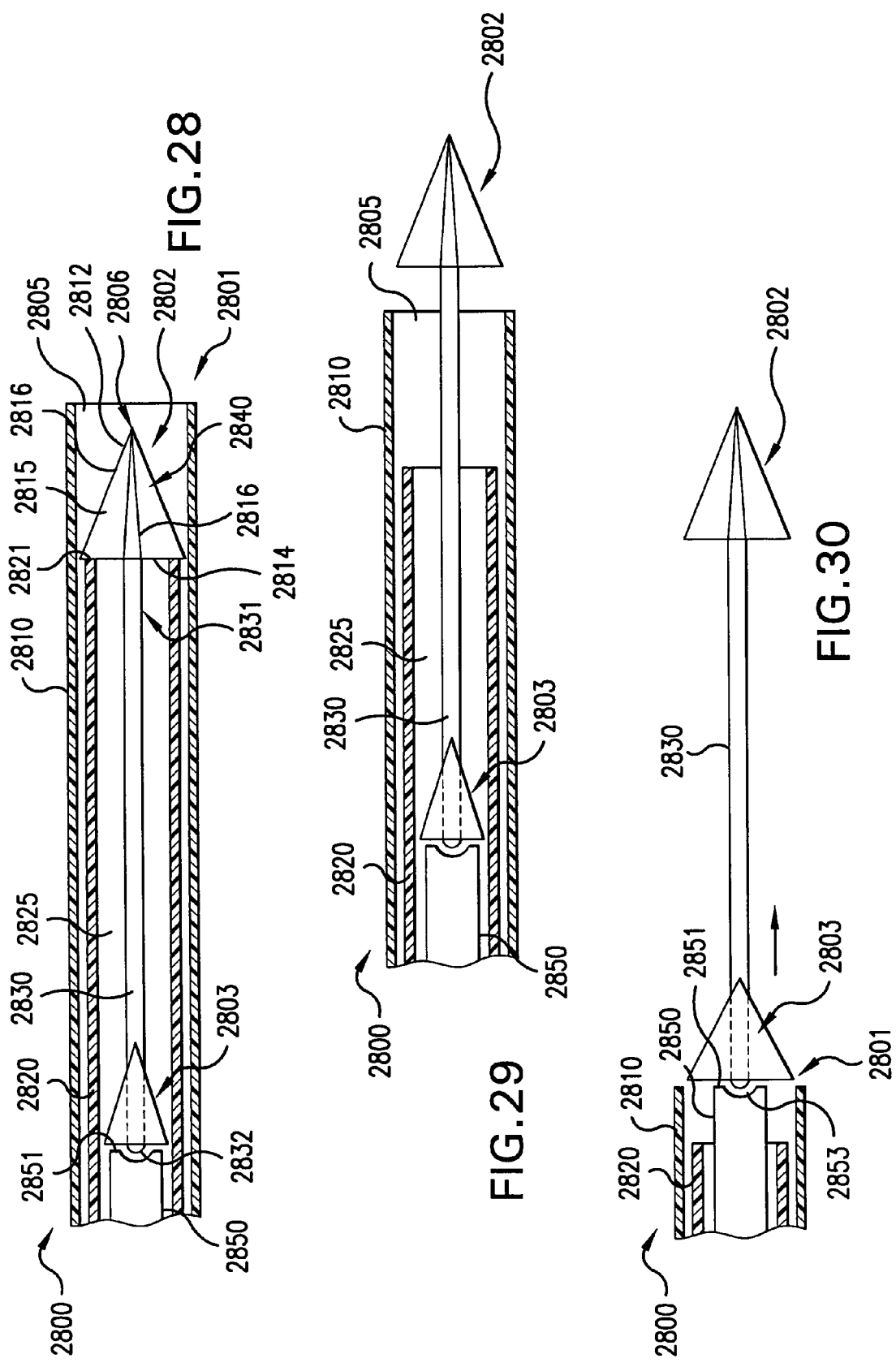

CATHETER WITH SENSOR TIPS, TOOL AND DEVICE AND METHODS OF USE OF SAME

CROSS REFERENCE TO RELATED PATENT APPLICATION

The present application claims the benefit of priority of U.S. Provisional Patent Application No. 60/556,059, filed Mar. 25, 2004.

FIELD OF THE INVENTION

Embodiments of the present invention relate to catheter-based sensors and methods for the injection of therapeutic and other agents at a target site within a patient's body. More particularly, the embodiments relate to catheter-based injection systems with electric sensors.

BACKGROUND

Medical catheters are used for innumerable minimally invasive medical procedures. Catheters may be used, for example, for delivery of therapeutic drug doses to target tissue and/or for delivery of medical devices such as lumen-reinforcing or drug-eluting stents. Likewise, catheters may be used to guide medical instruments to a target site to perform a surgical procedure, such as tissue rescission, ablation of obstructive deposits or myocardial revascularization.

Currently, catheter-based systems that are equipped with sensors (for example, electrodes) have a sensor tip at the distal end of the catheter. The sensor tip may or may not have an opening to permit a needle or a medical device to pass through the opening and into target tissue in the patient. These systems usually have one or more additional return sensors implemented as bands circumferentially around the catheter. In some systems, tissue contact is determined by measuring the impedance between the tip sensor when it is in contact with tissue and a return sensor that is not in contact with the tissue but is only in contact with a fluid, for example, blood, that is surrounding the tissue. However, this determination is based on known, that is, pre-determined, impedance values when the electrode is in contact with tissue and when only in contact with body fluids (for example, blood). Unfortunately, this method is not without problems, since the impedances of tissue and body fluid (for example, blood) are known to change during a procedure and different tissue will have different impedances depending on whether the tissue is healthy or diseased.

Alternatively, other sensor systems using a tip sensor and one or more band sensors around the catheter determine tissue contact by measuring impedance between sensors when the sensors are both contacting the tissue. Consequently, for this type of catheter to be able to detect the impedance, it must be lying flat against the target tissue area so that at least two of the sensors are in contact with the tissue. Unfortunately, this position does not enable the optimal targeted delivery of therapeutic agents to provide the most effective treatment regimen, since the tissue determined to be the target is usually not directly in line with the tip of the catheter.

SUMMARY OF THE INVENTION

The invention is directed to improved catheter systems with sensors and related methods. In certain embodiments, a device and method are provided for injecting therapeutic and other fluids at a target site within a patient's body. The device may include a catheter with a distal end and a proximal end, at least one lumen extending therebetween, at least one needle extending the length of the lumen, and a sensor located at the distal end of the catheter to detect characteristic electrical signals. The sensor may have at least one opening co-axially aligned with the lumen to permit the at least one needle to extend through the opening and out of the catheter. The device may also include at least two sensor leads, a distal end of each of the sensor leads in electrical communication with the sensor, and a proximal end of each of the sensor leads extending to the catheter proximal end where they may be connected to a monitoring device, for example, an electrocardiogram (EKG).

Other aspects of the invention are set forth in the appended claims.

BRIEF DESCRIPTION OF THE DRAWINGS

The foregoing and further features and advantages of the invention will become apparent from the following description of preferred embodiments with reference to the accompanying drawings, wherein like numerals are used to represent like elements and wherein:

FIG. 18 is a cross-sectional side view of the distal end of a catheter with sensing electrodes and an expandable component to deliver a therapeutic, the expandable component in an unexpanded position, in accordance with an embodiment of the present invention.

FIG. 19 is a cross-sectional side view of the distal end of a catheter with sensing electrodes and an expandable component to deliver a therapeutic, the expandable component in an expanded position, in accordance with an embodiment of the present invention.

FIG. 20 is a front-end view of the distal end of the catheter of FIG. 19, in accordance with an embodiment of the present invention.

FIG. 21 is a front-end view of an alternative dual sensor configuration for the distal end of the catheter of FIG. 19, in accordance with another embodiment of the present invention.

FIG. 25 is a top view of an alternative three-wing tip anchor configuration of the wire in FIGS. 22 and 23 loaded in a wire deployment tool with the three-wing tips in a folded position and ready for insertion into a target tissue site, in accordance with an embodiment of the present invention.

FIG. 26 is a cross-sectional side view of the three-wing tip anchor and wire deployment tool of FIG. 25 showing the wing tips in their folded position within the wire deployment tool, in accordance with an embodiment of the present invention.

FIG. 27 is a cross-sectional side view of the tip and wire deployment tool of FIG. 25 showing the tip in an unfolded position outside the wire deployment tool, in accordance with an embodiment of the present invention.

FIG. 28 is a cross-sectional side view of a wire with a first tip and a second tip in the wire deployment tool of FIG. 25 showing both tips in their folded positions within a distal end of the wire deployment tool, in accordance with an embodiment of the present invention.

FIG. 29 is a cross-sectional side view of the wire and the wire deployment tool of FIG. 28 showing the first tip in an unfolded position extending past the distal end of the wire deployment tool, in accordance with an embodiment of the present invention.

FIG. 30 is a cross-sectional side view of the wire and the wire deployment tool of FIG. 28 showing both the first and second tips in unfolded positions extending past the distal end of the wire deployment tool, in accordance with an embodiment of the present invention.

DETAILED DESCRIPTION

Some embodiments of the present invention may include a needle-based direct injection device similar to, for example, a Stiletto catheter manufactured by Boston Scientific of Natick, Mass., with an electrode sensor tip. In some embodiments, the sensor tip may include at least two electrodes separated by an insulator and connected to a monitoring device, for example, an electrocardiogram (EKG) to permit the monitoring of electrical signals in tissue that is in contact with the electrodes. For example, if the sensor tip were placed at a specific location (e.g., the AV node of the heart), the sensor tip may read any distinct electrical patterns generated by the tissue. Therefore, the sensor tip may be used to locate a characteristic electrical pattern known to be associated with a specific tissue location and target the location for the injection of therapeutics.

It is believed that injecting certain therapeutic agents, for example, certain genetic substances, into the AV node of the heart may provide a superior treatment for certain arrhythmias, such as, bradyarrhythmia and ventricular tachyarrhythmia. Unfortunately, current treatments, for example, oral drugs, radio frequency ablation, and implantable devices lack the desired effectiveness and have undesirable side effects. Fortunately, direct injection of a therapeutic agent, for example, a gene therapy agent, into the target tissue may provide a significantly improved effectiveness and with fewer side effects.

Figure 1:
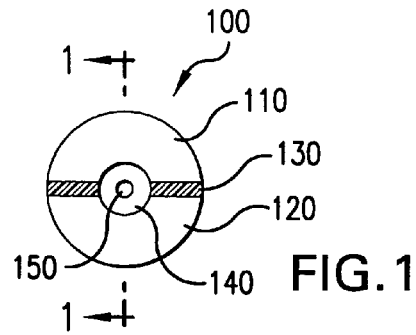
FIG. 1 is a front-end view of a distal end of a catheter with sensing electrodes, in accordance with an embodiment of the present invention.

FIG. 1 is a front-end view of a distal end of a catheter with sensing electrodes, in accordance with an embodiment of the present invention. In FIG. 1, a sensor 100 may include a first electrode 110 and a second electrode 120 with an insulator 130 between them to form a generally circular disk shape that may be affixed directly to a distal end of the catheter. Electrodes 110, 120 may be made of any electrically conductive material, for example, # 304 stainless steel or like conductive, surgical material and may be of sufficient thickness to prevent deformation of sensor 100 when it contacts tissue. Sensor 100 may have a smooth, a rough and/or a slightly adhesive surface on its distal end. The rough and slightly adhesive surfaces may help prevent sensor 100 from "jumping" off the tissue when the needle is deployed. In an alternate embodiment, sensor 100 may have small protrusions on its distal end that may penetrate or merely depress tissue when placed against the tissue to further help prevent sensor 100 from "jumping" off the tissue when the needle is deployed. Each of the jumping prevention embodiments may be particularly useful in locations that may experience significant movement of the tissue, for example, an AV node of the heart.

In FIG. 1, insulator 130 may include any non-conductive material or adhesive, for example, a urethane adhesive, having, but not limited to, a thickness of approximately 0.020 or more inches between electrodes 110, 120. For example, in addition to greater thickness, for example, 0.030 and 0.040 inches, insulator 130 may be of a thickness of less than 0.020 inches depending on the propensity of first electrode 110 and second electrode 120 to short circuit each other. Insulator 130 may also include TEFLON™ or a non-conductive plastic. Sensor 100 may also have an axially disposed opening 140 extending from its proximal surface to its distal surface for communication with and axially aligned with a lumen in the catheter. Opening 140 may be of sufficient diameter to permit the extension and retraction of a needle 150 through sensor 100 without contacting needle 150 against either first electrode 110 or second electrode 120. In accordance with embodiments of the present invention, sensor 100 may be manufactured and the sizing of opening 140 may be set by inserting a non-stick core, for example, TEFLON™, between first electrode 110 and second electrode 120 and sliding the two electrodes and non-stick core into a non-stick tube, for example, a TEFLON™ tube, having a predetermined internal diameter. Wicking and/or injecting the adhesive into the gap between electrodes 110, 120 may insert an adhesive, for example, an insulating adhesive. When the adhesive has set, sensor 100 may be removed from the non-stick tube, the non-stick core may be removed from opening 140, and any excess adhesive may be trimmed from sensor 100. Alternatively, first electrode 110 and second electrode 120 may have an adhesive applied to their respective opposing side faces and the non-stick core and one or more preformed insulating pieces may be assembled between first electrode 110 and second electrode 120 and then the entire assembly may be slid into the non-stick tube, or some other clamping device until the adhesive may set. Still further, other manufacturing techniques, including injection molding, may be used as well.

In FIG. 1, although the shape of sensor 100 may be shown in this embodiment as being generally circular, the shape is not determinative of how sensor 100 operates, and other embodiments are possible, for example, oval/ovoid, square and hemispherical shapes, some of which will be shown and detailed in subsequent figures and description. Insulator 130, for example, may be used to fix the electrodes 110, 120 together. Likewise, other embodiments are contemplated in which sensor 100 may be segmented into three or more electrodes that may be fixed to, but electrically insulated from, each other. Likewise, in accordance with an embodiment of the present invention, insulator 130 may extend around the inside of opening 140 to form an annular insulating band, which may further assure that needle 150 does not touch either first electrode 110 or second electrode 120. Alternatively, a separate insulator may be used for this purpose. Similarly, in accordance with an embodiment of the present invention, sensor 100 may be a single electrode with two or more spatially oriented lead wires attached thereto to act as a thermocouple detection device by measuring the impedance between the lead wires.

Figure 2:
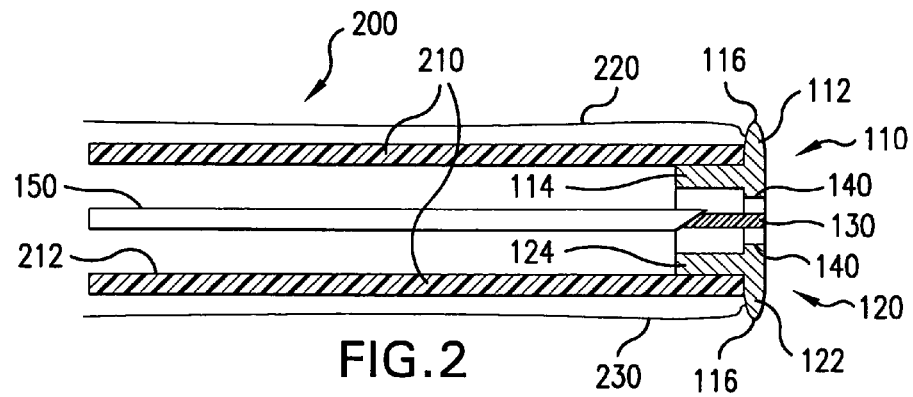
FIG. 2 is a cross-sectional side view of the distal end of the catheter of FIG. 1 along line 1-1, in accordance with an embodiment of the present invention.

FIG. 2 is a cross-sectional side view of the distal end of the catheter of FIG. 1 along line 1-1, in accordance with an embodiment of the present invention. In FIG. 2, first electrode 110 may include an end plate 112 and a generally semicircular, cylindrical wall 114 generally perpendicular to and extending proximally from a proximal side of end plate 112. End plate 112 may have an outer circular edge 116 that may be rounded to present a smooth, sliding surface for easy extension and retraction of the catheter from a patient. Likewise, second electrode 120 may include an end plate 122 and a generally semicircular, cylindrical wall 124 generally perpendicular to and extending proximally from a proximal side of end plate 122. Generally, semicircular, cylindrical wall portions 114, 124 may be separated from, and possibly affixed to, each other by a portion of insulator 130, which may extend proximally from the proximal sides of end plates 112, 122.

In FIG. 2, in accordance with an embodiment of the present invention, a sensor tip injection device 200 may include sensor 100, which, for example, may be affixed to the interior diameter of the distal end of a catheter 210, with catheter 210 having a lumen extending from a proximal end to the distal end. Alternatively, sensor 100 may be affixed to the exterior diameter of the distal end of catheter 210. Sensor 100 may be affixed to the distal end of catheter 210 with the same and/or different adhesive used to form insulator 130 (in those embodiments where insulator 130 is formed of adhesive), which may help to further insulate sensor 100 from the remainder of sensor tip injection device 200. Specifically, exterior sides of cylindrical walls 114, 124 of sensor 100 may be affixed to a catheter interior wall 212, which may define the lumen. A first lead wire 220 may extend from the proximal end of catheter 210 along the exterior wall of catheter 210 to the distal end of catheter 210 to be electrically coupled with first electrode 110. For example, first lead wire 220 may attach to the proximal side of end plate 112 of first electrode 110. Similarly, a second lead wire 230 may be similarly arranged and connected to a proximal side of end plate 122. First lead wire 220 and second lead wire 230 may each be attached to the exterior of catheter 210 along its length, at selected points, or not at all. In an embodiment of the present invention, lead wires 220, 230 may be of approximately 36-gauge wire, which may include copper and/or copper-clad stainless steel wire. Likewise, the wire may have a Polyimide insulation coating. In an embodiment of the present invention, a protective outer covering/sheathing (not shown) may enclose first lead wire 220 and second lead wire 230. The protective outer covering/sheathing may be, for example, a resin, a plastic and/or a heat shrink-wrap. The proximal ends of each of first lead wire 220 and second lead wire 230 may be connected to monitoring equipment, for example, an EKG monitor and/or a thermocouple monitor, to measure the electrical signals in the target tissue, for example, electrical signals indicative of bradyarrhythmia and/or ventricular tachyarrhythmia at the AV node of the heart.

In FIG. 2, although this embodiment shows a single needle sensor tip injection device with generally planar distal sides of end plates 112, 122, various other embodiments are contemplated which may include, for example, multiple needles and/or rounded sensors 100, which may have a slightly dome-like shape.

In FIG. 2, in accordance with an embodiment of the present invention, sensor tip injection device 200 may be used to identify a specific tissue location within a patient to deliver a therapeutic. For example, sensor tip injection device 200 may be located on the specific tissue location by moving sensor 100 until it detects a known/predetermined characteristic electrical signal for the desired specific tissue location thereby signifying contact. At this point, needle 150 may be actuated to extend through opening 140 in sensor 100 to enter the specific tissue location to deliver the therapeutic in exactly the desired location. Alternate embodiments of needle 150 are also contemplated to overcome the potential loss of therapeutic at the injection site. For example, needle 150 may have a helical or a corkscrew-like shape that may be inserted into the specific tissue location to produce a deeper/longer needle hole, which may result in more of the therapeutic being retained in the tissue. In yet another embodiment to minimize the loss of therapeutic at the injection site, needled 150 may include a solid therapeutic, for example, a polymer and cells, that may break-off in predetermined lengths when the needle is extended beyond the distal end of catheter 210 and into the target tissue.

Figure 3:
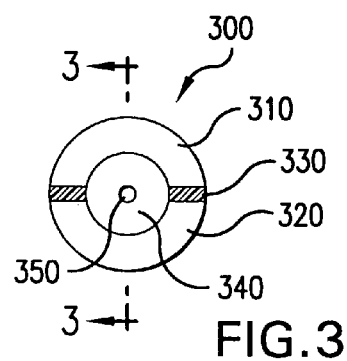
FIG. 3 is a front-end view of a distal end of a catheter with sensing electrodes, in accordance with another embodiment of the present invention.

FIG. 3 is a front-end view of a distal end of another embodiment of the catheter in FIG. 1. In FIG. 3, a sensor 300 may include a first electrode 310 and a second electrode 320 that may be separated from, and possibly fixed to, each other by an insulator 330, to form a generally circular disk shape that may be affixed directly to a distal end of the catheter. As with sensor 100 in FIG. 1, in FIG. 3, electrodes 310, 320 may be made of any electrically conductive material, for example, # 304 stainless steel or like conductive, surgical material, and may be of sufficient thickness to prevent deformation of sensor 300 when it contacts tissue. Insulator 330 also may include any non-conductive adhesive, for example, a urethane adhesive, having, but not limited to, a thickness of approximately 0.020 or more inches between electrodes 310, 320. For example, insulator 330 may be of similar manufacture as described above in relation to sensor 100. Again, similar to sensor 100 in FIG. 1, in FIG. 3, sensor 300 may have an axially disposed opening 340 extending from its proximal surface to its distal surface for communication with and axially aligned with a lumen in the catheter. In sensor 300, opening 340 is shown as being larger than opening 140 in sensor 100. In another embodiment of the present invention, opening 340 in sensor 300 may be smaller than opening 140 in sensor 100. Regardless, opening 340 may be of sufficient diameter to permit the extension and retraction of at least one needle 350 through sensor 300 without contacting either first electrode 310 or second electrode 320.

In FIG. 3, although the shape of sensor 300 may be shown in this embodiment as being generally circular, the shape is not determinative of how sensor 300 may operate, and other embodiments are possible, for example, oval/ovoid, square and hemispherical shapes, some of which will be shown and detailed in subsequent figures and description. As with sensor 100, other embodiments are contemplated in which sensor 300 may be segmented into three or more electrodes that may be fixed to, but electrically insulated from, each other by insulator 330. Likewise, in accordance with an embodiment of the present invention, insulator 330 may extend around the inside of opening 340 to form an annular insulating band (not shown), which may further assure that needle 350 does not touch either first electrode 310 or second electrode 320 and cause a short in the signal from either electrode. Alternatively, a separate insulator may be used for this purpose. Similarly, in accordance with an embodiment of the present invention, sensor 300 may be a single electrode with two or more spatially oriented lead wires attached thereto to act as a thermocouple detection device by measuring the impedance between the lead wires.

Figure 4:
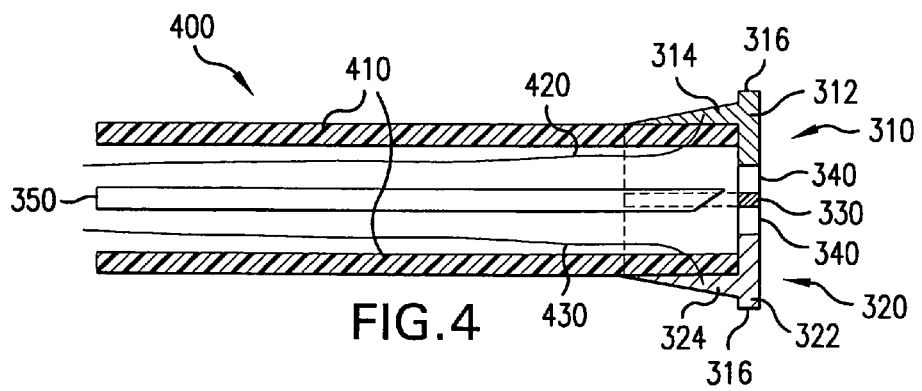
FIG. 4 is a cross-sectional side view of the distal end of the catheter of FIG. 3 along line 3-3, in accordance with an embodiment of the present invention.

FIG. 4 is a cross-sectional side view of the distal end of the catheter of FIG. 3 along line 3-3, in accordance with an embodiment of the present invention. In FIG. 4, a sensor tip injection device 400 may include first electrode 310 and second electrode 320, which may each include an end plate 312, 322 and a tapered, generally semicircular, cylindrical wall 314, 324 generally perpendicular to and extending proximally from a proximal side of each end plate 312, 322, respectively. End plates 312, 322 may have an outer circular edge 316 that may be generally square in cross-sectional profile in order to provide a substantially planar contacting surface of end plates 312, 322. Other embodiments are contemplated in which, for example, outer circular edge 316 also may be rounded as in sensor 100, or only slightly rounded over at the corners of circular edge 316, or rounded over from the distal side of end plates 312, 322 to the proximal side of end plates 312, 322, etc. Generally semicircular, cylindrical wall portions 314, 324 may be separated from, and possibly affixed to, each other by a portion of insulator 330 (shown as hidden lines), which may extend proximally from end plates 312, 322. An exterior edge of each of generally semicircular, cylindrical wall portions 314, 324 may each be tapered away from their respective end plates 312, 322 toward the exterior side wall of catheter 410 to form a wedge-like shape.

In FIG. 4, sensor tip injection device 400 may include sensor 300, which may be affixed to an outside diameter of the distal end of a catheter 410, with catheter 410 having a lumen extending from a proximal end to the distal end of catheter 410. Alternatively, sensor 300 may be affixed to the interior diameter of the distal end of catheter 410. In such an embodiment, the tapering of semicircular, cylindrical wall portions 314, 324 may be reversed to taper away from the central axis of opening 340 to the interior wall of catheter 410. Such a configuration may aid in guiding and centering needle 350 when it is extended through opening 340. Sensor 300 may be affixed to the distal end of catheter 410 with the same and/or different adhesive used to form insulator 330 (in cases where insulator 330 is formed of adhesive), which may help to further insulate sensor 300 from the remainder of sensor tip injection device 400. Specifically, interior sides of cylindrical walls 314, 324 of sensor 300 may be affixed to an exterior wall of catheter 410. The opposite, interior wall of catheter 410 may define the lumen that extends from the proximal end to the distal end of catheter 410.

In FIG. 4, a first lead wire 420 and a second lead wire 430 may extend from the proximal end of catheter 410 along the interior wall of catheter 410 and through the interior wall of the distal end to be electrically coupled with first electrode 310 and second electrode 320, respectively. For example, first lead wire 420 may couple to cylindrical wall 314 of end plate 312, and second lead wire 430 may attach to cylindrical wall 324 of end plate 322. First lead wire 420 and second lead wire 430 may each be attached to the interior lumen walls of catheter 410 along its length, at selected points, or not at all. In another embodiment of the present invention, first lead wire 420 may be coupled to the proximal side of first electrode end plate 312 that may overhang the distal end of catheter 410, and second lead wire 430 may be coupled to the proximal side of second electrode end plate 322 that may overhang the distal end of catheter 410. In embodiments of the present invention, each lead wire 420,430 may be directly coupled to their respective electrodes 310, 320 through the interior of catheter 410 or by passing through the interior lumen walls at the distal end of catheter 410 and then into electrodes 310, 320, respectively.

In FIG. 4, like FIG. 1, the embodiment shows only a single needle sensor tip injection device with generally planar distal sides of sensor end plates 312, 322, but various other embodiments are contemplated which may include, for example, multiple needles and/or rounded sensors 300, which may include end plates having a slightly dome-like shape.

Similar to sensor tip injection device 200, in accordance with an embodiment of the present invention, in FIG. 4, sensor tip injection device 400 may be used to identify a specific tissue location within a patient to deliver a therapeutic. For example, sensor tip injection device 400 may be located over the specific tissue location by moving sensor 300 until the distal sides of end plates 312, 322 detect a known/ predetermined characteristic electrical signal for the desired specific tissue location, thereby signifying contact. At this point, needle 350 may be actuated to extend through opening 340 in sensor 300 to enter the specific tissue location to deliver the therapeutic in exactly the desired location. As in FIG. 2, alternate embodiments of needle 350 are also contemplated to overcome the potential loss of therapeutic at the injection site. For example, needle 350 may have a helical and/or a corkscrew-like shape that may be inserted into the specific tissue location to produce a deeper/longer needle hole, which may hold more of the therapeutic in the tissue.

Figure 5:
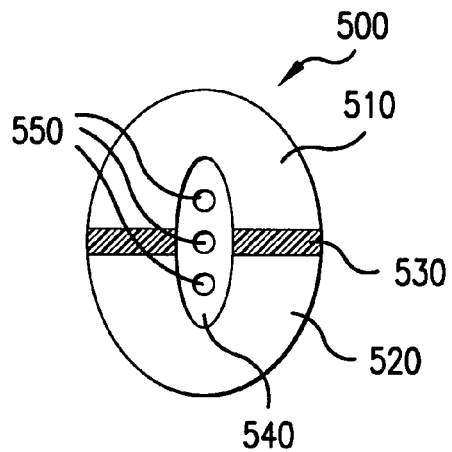
FIG. 5 is a front-end view of a distal end of a catheter with sensing electrodes, in accordance with yet another embodiment of the present invention.

FIG. 5 is a front-end view of a distal end of a catheter with sensing electrodes, in accordance with another embodiment of the present invention. In FIG. 5, a sensor 500 may include a first electrode 510 and a second electrode 520 with an insulator 530 between them to form a generally oval shape. In addition, an opening 540 may be located in sensor 500 and may be of a generally oval shape to permit one or more needles 550 to be introduced through opening 540. For example, in the embodiment of the present invention shown in FIG. 5, opening 540 may be substantially axially aligned with the center of sensor 500 and may accommodate multiple, for example, three, needles 550. However, alternative embodiments are contemplated in which less than three as well as more than three needles may be used. Regardless of the number of needles, in accordance with embodiments of the present invention, this and all multiple lumen, for example, needle and/or needle-less, designs may be used to polymerize two or more therapeutic agents upon injection. This may be accomplished by keeping each of the therapeutic agents from mixing until they are injected and/or delivered to the tissue. In the needle-less embodiments, the therapeutic may be delivered to but not injected into the target tissue.

In FIG. 5, although not shown, sensor 500 may also have perpendicular and proximally extending walls similar to cylindrical walls 114, 124 in FIG. 2 and cylindrical walls 314, 324 in FIG. 4 to fit into or over the distal end of a catheter. Alternative shapes are contemplated including, for example, oval and/or square.

Figure 6:
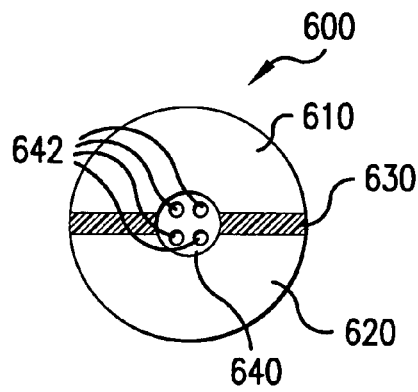
FIG. 6 is a front-end view of an alternative distal end configuration of a catheter with sensing electrodes, in accordance with yet another embodiment of the present invention.

FIG. 6 is a front-end view of an alternative distal end configuration of a catheter with sensing electrodes, in accordance with yet another embodiment of the present invention. In FIG. 6, a sensor 600 may include a first electrode 610 and a second electrode 620 separated and possibly fixed together by an insulator 630 to form a generally circular shape. In addition, an opening 640 may be located substantially axially aligned with a center of sensor 600, may be of a generally circular shape and may be substantially filled with insulator 630 in which one or more openings 642 may be placed to permit one or more needles (not shown) to be introduced through one or more openings 642. Insulator 630 may not only insulate any needles that may pass through one or more openings 642, but also may provide one or more guides and added stability for the needles. For example, in the embodiment of the present invention shown in FIG. 6, sensor 600 may accommodate up to four needles. However, other embodiments are contemplated in which less than four as well as more than four openings may be disposed in the sensor.

Similar to FIG. 5, in FIG. 6, although not shown, sensor 600 may also have generally perpendicular and proximally extending walls similar to walls 114, 124 in FIG. 2 and walls 314, 324 in FIG. 4 to fit into or over the distal end of a catheter. Alternative shapes are contemplated including, for example, oval and/or square.

Figure 7:
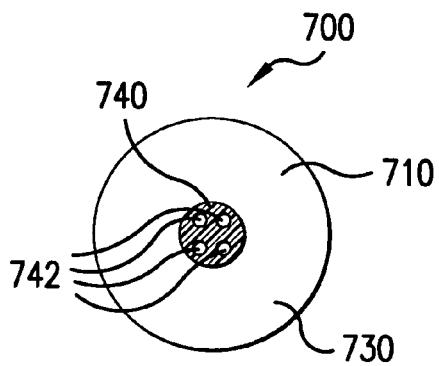
FIG. 7 is a front-end view of an alternative distal end configuration of a catheter with sensing electrodes, in accordance with yet another embodiment of the present invention.

FIG. 7 is a front-end view of an alternative distal end configuration of a catheter with sensing electrodes, in accordance with yet another embodiment of the present invention. In FIG. 7, a sensor 700 may include a single electrode 710, with an insulator 730 disposed in an opening 740 in single electrode 710. Single electrode 710 may be in a generally circular shape, and opening 740 also may be of a generally circular shape and may be located substantially axially aligned with a center of single electrode 710. In addition, insulator 730 may include one or more openings 742 to permit one or more needles (not shown) to be introduced through one or more openings 742. Insulator 730 may not only insulate any needles that may pass through the one or more openings 742, but may also provide one or more guides and added stability for the needles. For example, in the embodiment of the present invention shown in FIG. 7, sensor 700 may accommodate up to four needles. However, alternative embodiments are contemplated in which less than four as well as more than four openings may be disposed in sensor.

Similar to FIGS. 5 and 6, in FIG. 7, although not shown, sensor 700 may also have one or more generally perpendicular and proximally extending walls similar to walls 114, 124 in FIG. 2 and walls 314, 324 in FIG. 4 to fit into or over the distal end of a catheter. Alternative shapes are contemplated including, for example, oval and/or square.

Figure 8:
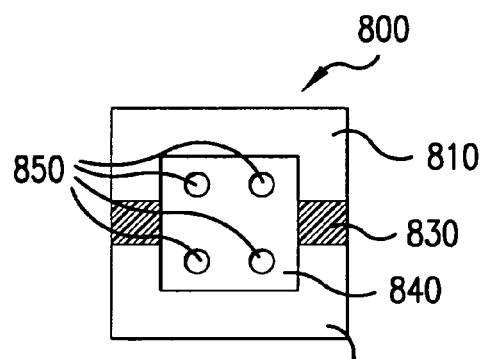
FIG. 8 is a front-end view of an alternative distal end configuration of a catheter with sensing electrodes, in accordance with yet another embodiment of the present invention.

FIG. 8 is a front-end view of an alternative distal end configuration of a catheter with sensing electrodes, in accordance with yet another embodiment of the present invention. In FIG. 8, a sensor 800 may include a first electrode 810 and a second electrode 820 fixed together by an insulator 830 to form a generally square shape. In addition, an opening 840 in sensor 800 may be of a generally square shape to permit one or more needles to be introduced through opening 840. For example, in the embodiment of the present invention shown in FIG. 8, four needles 850 are shown. However, alternative embodiments are contemplated in which less than four as well as more than four needles may be used. In another embodiment of the present invention, sensor 800 may include a substantially square shape with rounded corners and/or edges to permit easier movement into and out of a patient's body.

Similar to FIGS. 5 through 7, in FIG. 8, although not shown, sensor 800 may also have generally perpendicular and proximally extending walls similar to walls 114, 124 in FIG. 2 and walls 314, 324 in FIG. 4 to fit into or over the distal end of a catheter. Alternative shapes are contemplated including, for example, oval and/or square.

Figure 9:
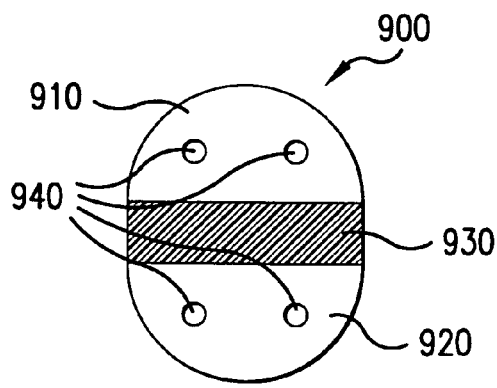
FIG. 9 is a front-end view of an alternative distal end configuration of a catheter with sensing electrodes, in accordance with yet another embodiment of the present invention.

FIG. 9 is a front-end view of an alternative distal end configuration of a catheter with sensing electrodes, in accordance with another embodiment of the present invention. In FIG. 9, a sensor 900 may include a first electrode 910 and a second electrode 920 separated and possibly fixed together by an insulator 930 running therebetween to form a substantially oval shape. In addition, one or more openings 940 may be located in first electrode 910 and/or second electrode 920 to permit one or more needles to be introduced through one or more openings 940. In this embodiment, insulator 930 may insulate only first electrode 910 and second electrode 920 from each other. Any needles that pass through the one or more openings 940 may be non-conductive or, alternatively, may be further insulated from first and/or second electrodes 910, 920 by an insulating coating that may be applied to the interior walls defining each of one or more openings 940 or to the needles. One or more openings 940 may also provide added stability for any needles that may pass through the one or more openings 940. For example, in the embodiment of the present invention shown in FIG. 9, sensor 900 may accommodate up to four needles. However, other embodiments are contemplated in which less than four as well as more than four openings may be disposed in the sensor. In other embodiments of the present invention, one or more openings 940 may be disposed in insulator 930 and/or any combination of one or more openings 940 in electrodes 910, 920 and insulator 930.

Similar to FIGS. 5 through 8, in FIG. 9, although not shown, sensor 900 may also have generally perpendicular and proximally extending walls similar to walls 114, 124 in FIG. 2 and walls 314, 324 in FIG. 4 to fit into or over the distal end of a catheter. Alternative shapes are contemplated including, for example, oval and/or square.

Figure 10:
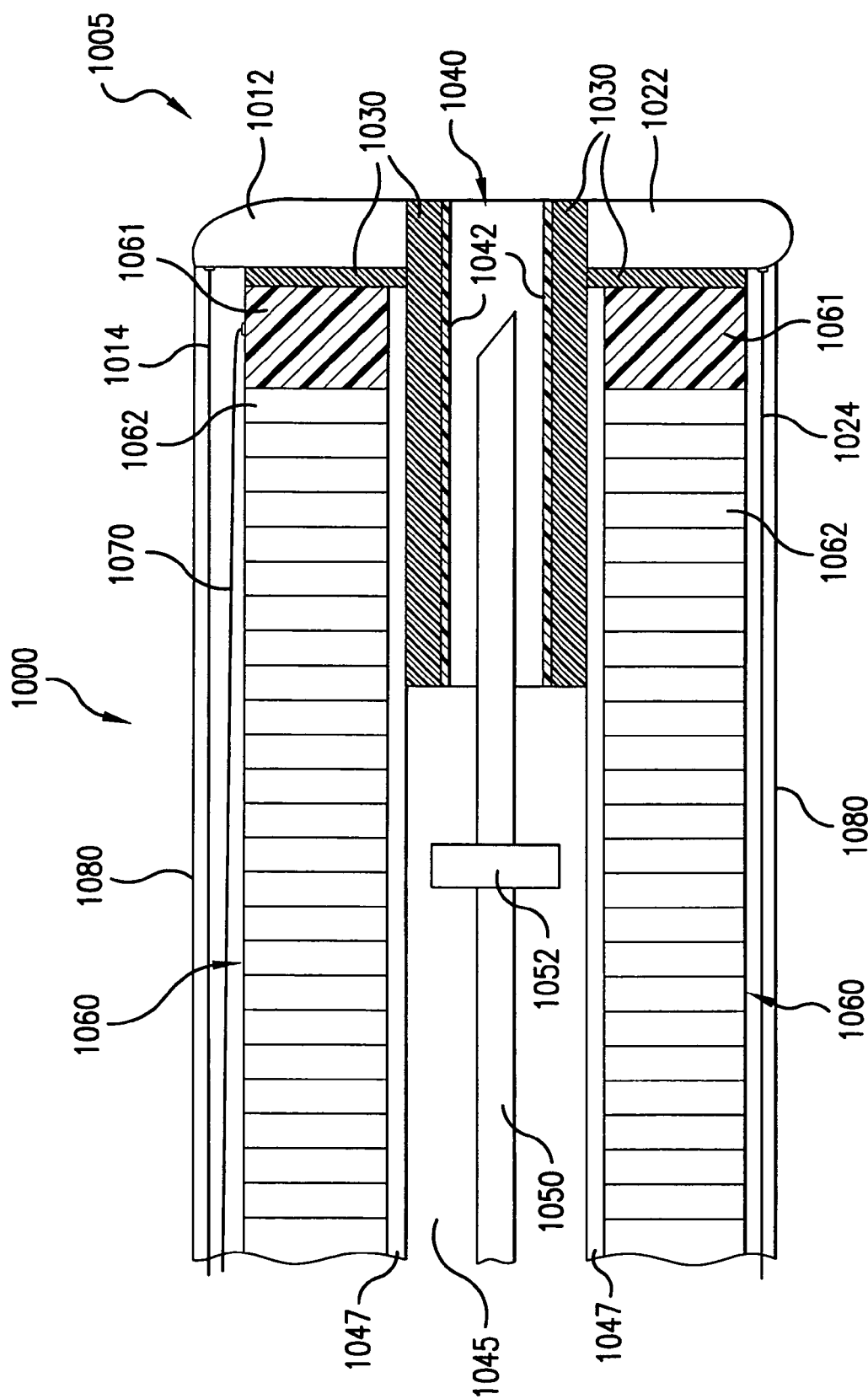
FIG. 10 is a cross-sectional side view of a distal end of a deflectable tip catheter with sensing electrodes, in accordance with an embodiment of the present invention.

FIG. 10 is a cross-sectional side view of a distal end of a deflectable tip catheter with sensing electrodes, in accordance with an embodiment of the present invention. In FIG. 10, a distal end of a deflectable tip catheter 1000 may include a sensor 1005 having a first electrode 1012 and to a second electrode 1022. Sensor 1005 may be a substantially circular disk without any proximally extending walls as in sensors 100 and 300 of FIG. 1 and FIG. 3, respectively. First electrode 1012 may be coupled to a first lead wire 1014, which may run from a proximal end to a distal end of deflectable tip catheter 1000, and second electrode 1022 may be coupled to a second lead wire 1024, which also may run from the proximal end to the distal end of deflectable tip catheter 1000. First electrode 1012 and second electrode 1022 may be separated, and possibly fixed to each other, by an insulator 1030. Consequently, first electrode 1012 and second electrode 1022 may be electrically insulated from each other. For example, sensor 1005 may be similar to sensor 600 from FIG. 6, except that in the present embodiment in FIG. 10, sensor 1005 is illustrated as having a single opening 1040 with a single needle 1050. Sensor 1005 also may be of any other suitable configuration, such as one of the configurations described or discussed above in relation to FIGS. 1 through 9. A proximal surface of sensor 1005 may be fixed at the distal end of deflectable tip catheter 1000, for example, by using insulator 1030, which may be seen to extend substantially perpendicularly and proximally from the distal surface of sensor 1005 through opening 1040 and into a lumen 1045 that runs from the proximal end to the distal end of catheter 1000. Lumen 1045 may be defined by an interior surface of an inner catheter wall 1047, which may also run from the proximal end to the distal end of catheter 1000. In addition, sensor 1005 may be fixed at the distal end of catheter 1000 by another portion of insulator 1030, which may be disposed proximal to the proximal surface of sensor 1005. Although first electrode 1012 and second electrode 1022 may be seen to have different configurations in FIG. 10, their shapes are merely illustrative of some of the possible electrode configurations of sensor 1005. The specific size and shape of first electrode 1012 and second electrode 1022 may be varied.

In FIG. 10, opening 1040 may include an interior lining 1042 fixed to the interior surface of the substantially proximally extending portion of insulator 1030. Interior lining 1042 may be a heat shrink material that may coat/adhere to the interior wall of the substantially proximally extending portion of insulator 1030 to provide additional insulation and an improved sliding surface for needle 1050. As seen in FIG. 10, needle 1050 may extend from the proximal end to the distal end of catheter 1000 and have a send marker band 1052 encircling a portion of needle 1050 near a distal end of needle 1050. Send marker band 1052 may have a substantially annular shape with a size corresponding to that of opening 1040. As a result, when needle 1050 is extended into and out of opening 1040, send marker band 1052 may slide into and out of opening 1040 to guide needle 1050 through and to provide support for needle 1050 in opening 1040. Send marker band 1052 may include a non-conducting material to insulate needle 1050 from sensor 1005. Send marker band 1052 may also act as a depth send for needle 1050 to prevent needle 1050 from extending too far into the target tissue. For example, if the distal side of sensor 1005 is in contact with the target tissue, the extension of needle 1050 may be limited by send marker band 1052 when it contacts the target tissue at the distal side of opening 1040.

In FIG. 10, in accordance with an embodiment of the present invention, catheter 1000 may include a deflection coil 1060 that may be fixed to the exterior side of inner catheter wall 1047 to enable the distal end of catheter 1000 to be selectively deflected. At least one pull/push wire 1070 may be attached to an exterior surface of deflection coil 1060 near sensor 1005 to enable the selective deflection of the distal end of catheter 1000. Deflection coil 1060 may be annular in shape including a solid cell ring 1061 located at the distal end of deflection coil 1060 and multiple compressive cells 1062 located proximal to solid cell ring 1061. The multiple compressive cells 1062 may be in a non-compressed state at rest and may compress and/or expand in response to the pulling or pushing of at least one pull/push wire 1070, which may be attached to solid cell ring 1061. Solid cell ring 1061, generally, may be made of a non-compressive material to provide a strong and stable anchoring point for at least one pull/push wire 1070. Each of the multiple compressive cells 1062 may include a material that may have a memory to help return the compressive cell back to its uncompressed state when deflection coil 1060 is un-deflected. For example, in an embodiment of the present invention, distal ends of four pull/push wires 1070 may be equidistantly fixed to and around the exterior surface of deflection coil 1060 on solid cell ring 1061 to provide four-way directional control of the distal end of catheter 1000. An exterior casing 1080 may run from the proximal end to the distal end of catheter 1000 and be fixed to an outer edge of the proximal side of sensor 1005 to enclose but not bind lead wires 1014, 1024 and one or more pull/push wires 1070. Use of deflection coil 1060 to control the position of the distal end of catheter 1000 enables sensor 1005 to be more easily positioned directly over and against the target tissue site that is to be treated.

In the embodiment in FIG. 10, the four pull/push wires 1070 may be separated by approximately 90° to permit a single pull/push wire 1070 to control movement in a single direction, for example, 0°, 90°, 180° and 270°; or up, right, down and left; or north, east, south and west; or 12, 3, 6 and 9 o'clock. Also, in this embodiment, simultaneously pulling or pushing on two adjacent pull/push wires 1070 may control the movement of the distal end of catheter 1000 in two directions to move the distal end of catheter 1000 between two adjacent pull/push wires 1070; for example, pulling equally on both the north and west pull/push wires 1070 may result in movement in the northwest direction (that is, half-way between 10 and 11 o'clock). Similarly, pulling twice as hard on the north wire as on the west wire may result in movement in the north, northwest direction (that is, 11 o'clock). Of course, it is to be understood that the above directions are relative to the position of the distal end of catheter 1000, which may have changed from its original position before being inserted into a lumen in a patient.

Alternatively, in FIG. 10, deflection coil 1060 may include two 180° arcs that may be disposed under first electrode 1012 and second electrode 1022. Accordingly, one or more pull/push wires 1070 may be attached to each arc of the deflection coil 1060 to permit the separate control of each deflection coil arc, as described above. Similarly, deflection coil 1060 may include multiple arcs with one or more pull/push wires 1070 disposed under the electrodes and around the exterior of inner catheter wall 1047. In embodiments with sensor 1005 having more than two electrodes, separate arcs may be disposed under each electrode to permit the selective deflection of sensor 1005.

Figure 11:
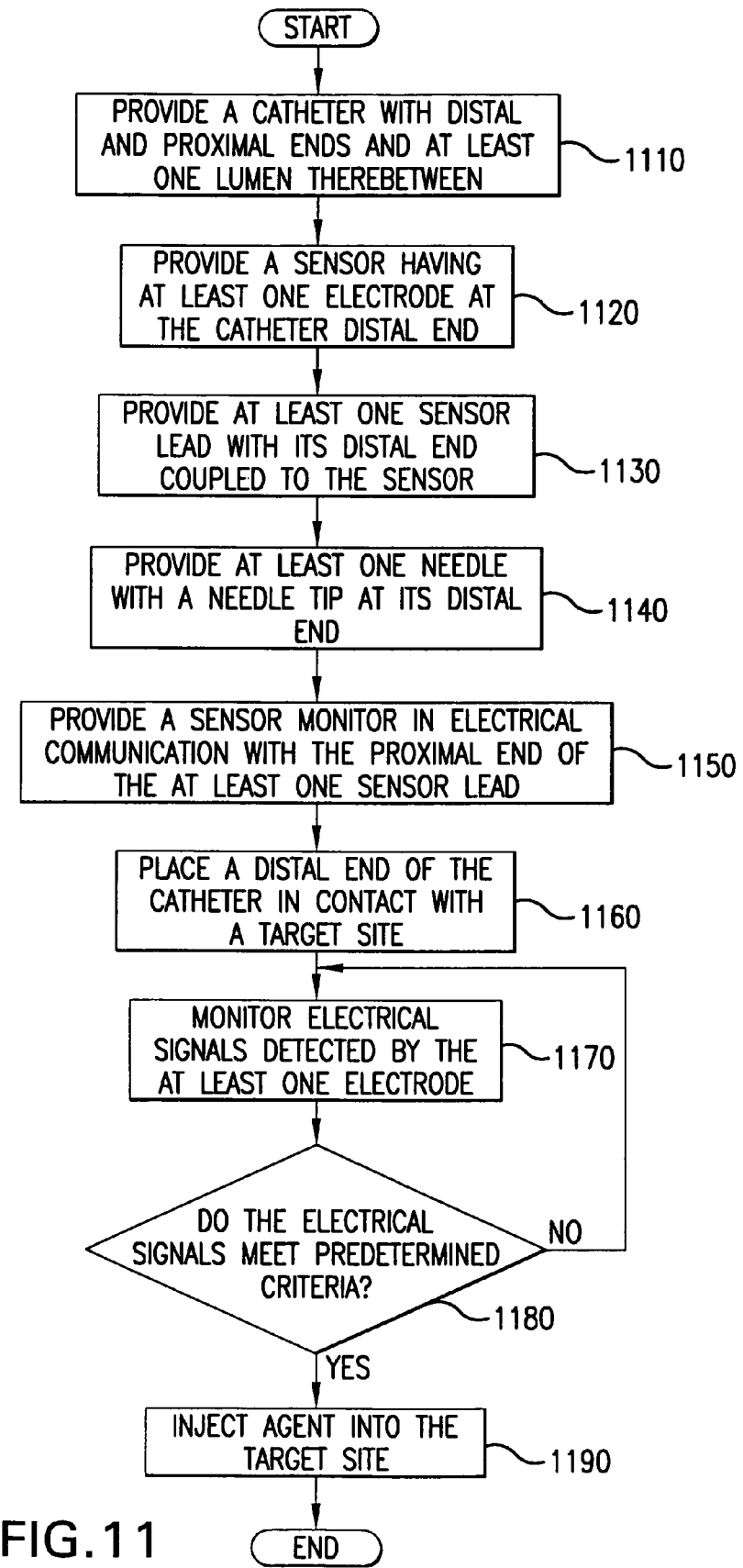
FIG. 11 is a flow diagram of a method for performing a sensor-guided catheter-based injection, in accordance with an embodiment of the present invention.

FIG. 11 is a flow diagram of a method for performing a sensor-guided catheter-based injection, in accordance with an embodiment of the present invention. In FIG. 11, the method may include providing (1110) a catheter with a distal end and a proximal end and at least one lumen extending therebetween. The method also may include providing (1120) a sensor located at the catheter distal end, the sensor including at least one electrode, the electrode being located at the catheter distal end such that the electrode may contact a target site when the catheter distal end is placed at the target site. The sensor may also include at least two electrodes and an insulator to electrically insulate the at least two electrodes from one another. The method may include providing (1130) at least one sensor lead, a distal end of each at least one sensor lead may be in electrical communication with a corresponding sensor, and a proximal end of each at least one sensor lead may extend to the catheter proximal end. The method may further include providing (1140) at least one needle having a distal end in the form of a needle tip and a proximal end adapted to receive a fluid injection, the at least one needle may be slidably disposed in one of the at least one catheter lumens between a retracted position in which the needle tip is within the catheter distal end and an extended position in which the needle tip is extended beyond the catheter distal end, the at least one needle may be electrically insulated from the at least one electrode. The method may also include providing (1150) a sensor monitor in electrical communication with the proximal end(s) of the at least one sensor lead to monitor electrical signals from the at least one electrode. The method may further include placing (1160) a distal end of the catheter in contact with a target site within a patient's body. The method may include monitoring (1170) electrical signals detected by the electrode(s) and determining (1180) whether the electrical signals detected by the electrode(s) meet a predetermined injection criteria. The method may continue monitoring (1170) the electrical signals, if the electrical signals do not meet the predetermined injection criteria. The method may include injecting (1190) an agent, for example, a therapeutic agent, into the target site and the method may end, if the electrical signals detected by the electrode(s) meet the predetermined injection criteria.

Figure 12:
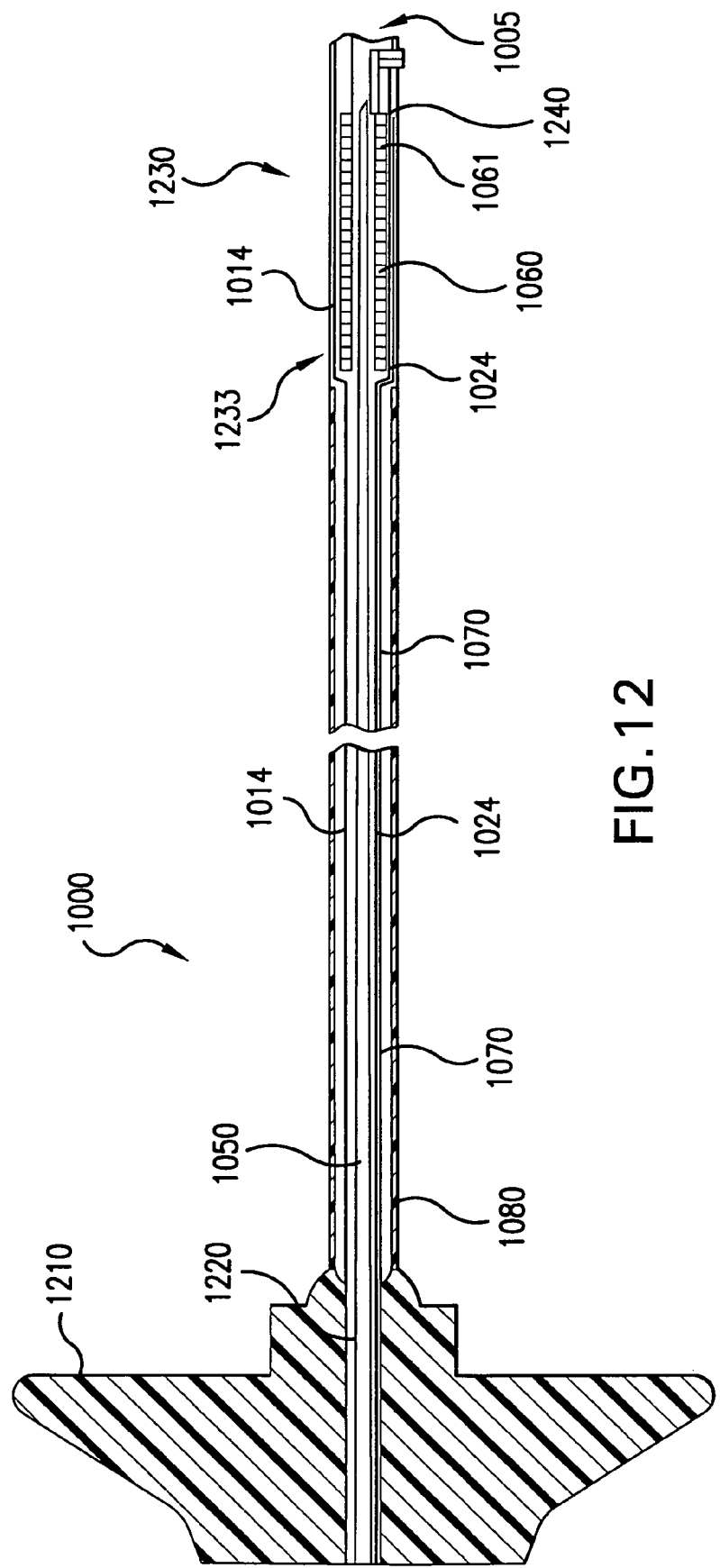
FIG. 12 is a cross-sectional side view of a deflectable tip catheter, in accordance with an embodiment of the present invention

FIG. 12 is a cross-sectional side view of a deflectable tip catheter, in accordance with an embodiment of the present invention. In FIG. 12, catheter 1000 may include a push/pull deflectable tip actuator 1210 with a lumen 1220 extending from a proximal end to a distal end of push/pull deflectable tip actuator 1210. A distal end of lumen 1220 may be co-axially aligned with a proximal end of lumen 1045 of catheter 1000 to form a continuous lumen from a proximal end of lumen 1220 to the distal end of lumen 1045. Push/pull deflectable tip actuator 1210 may be attached to the proximal end of catheter 1000 using, for example, an adhesive. Push/pull deflectable tip actuator 1210 may also be attached to the proximal end of push/pull wire 1070, and a distal end of push/pull wire 1070 may be attached near the distal end of catheter 1000 at a distal end of a deflectable tip 1230 of catheter 1000. Deflectable tip 1230 may be deflected in a predetermined direction, by manually pushing/pulling a distal side of push/pull deflectable tip actuator 1210. The amount of deflection may be controlled by the amount of force exerted against push/pull deflectable tip actuator 1210. Deflectable tip 1230 may deflect from its proximal end 1233 as a result of where push/pull wire 1070 may be attached at, for example, a solder joint 1240, to solid cell ring 1061 in deflectable tip 1230. In general, the pushing/pulling may be applied by a surgeon's hands and/or fingers. In other embodiments of the present invention, two or more push/pull wires 1070 may be attached at their respective proximal ends to push/pull deflectable tip actuator 1210 and at their distal ends to the deflectable tip 1230.

As illustrated in FIG. 12, distal ends of first lead wire 1014 and second lead wire 1024 may be attached to a proximal end of sensor 1005 and may extend proximally away from sensor 1005 and through lumen 1220 of push/pull deflectable tip actuator 1210.

A more detailed description of the operation of a deflectable tip catheter and a control assembly may be found in U.S. Pat. No. 6,083,222, issued on Jul. 4, 2000 and entitled "Deflectable Catheter for Ablating Cardiac Tissue," which is hereby incorporated by reference in its entirety.

Figure 13:
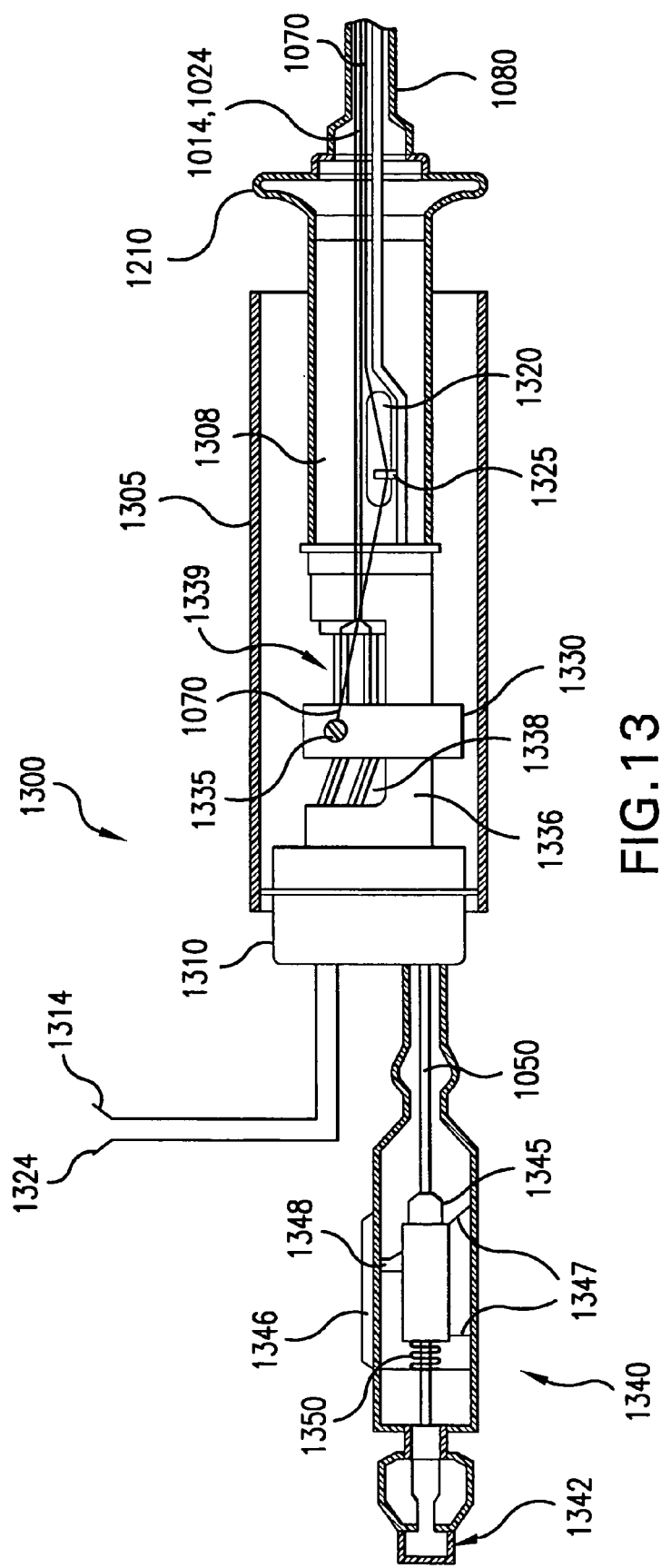
FIG. 13 is a cross-sectional, cut-away side view of the proximal end of the deflectable tip catheter of FIG. 12 with attached control mechanisms for elements in the deflectable tip catheter, in accordance with an embodiment of the present invention.

FIG. 13 is a cross-sectional, cut-away side view of the proximal end of the deflectable tip catheter of FIG. 12 with attached control mechanisms for elements in the deflectable tip catheter, in accordance with an embodiment of the present invention. In FIG. 13, control assembly may include a manifold 1305 having a proximal end and a distal end. The distal end of a manifold 1305 may be attached to the proximal end of push/pull deflectable tip actuator 1210 and first lead wire 1014 and second lead wire 1024 may be seen to extend through a coaxial lumen 1308 of the control assembly 1300 and out of a manifold cap 1310 in a proximal end of manifold 1305. The proximal ends of first lead wire 1014 and second lead wire 1024 may be connected to electrical signal monitoring equipment to display any electrical signals measured by sensor 1005.

In FIG. 13, in accordance with an embodiment of the present invention, control assembly 1300 may be fixedly and/or removably attached to push/pull deflectable tip actuator 1210. Push/pull wire(s) 1070 may extend proximally from deflectable tip 1230 of catheter 1000 through lumen 1308 around a tension bar 1320 with a tension post 1325 and terminate by attaching to a push/pull wire anchor 1330 in control assembly 1300. Specifically, the proximal ends of push/pull wire(s) 1070 may be anchored by, for example, a screw 1335, to push/pull wire anchor 1330. Push/pull wire anchor 1330 may be proximally biased to place push/pull wire(s) 1070 under tension between push/pull wire anchor 1330 and push/pull actuator 1210. Push/pull wire(s) 1070 may be used to control the amount of deflection of deflectable tip 1230 of catheter 1000 by activating push/pull actuator 1210. Push/pull wire anchor 1330 may be slidably engaged to a slide assembly 1336, which may be rigidly attached to an interior distal side of manifold cap 1310 at the proximal end of control assembly 1300. Slide assembly 1336 may include a lumen 1338 extending from its proximal end to its distal end through which sensor leads 1314, 1324 and needle 1050 may pass. Lumen 1338 may be axially aligned with and in communication with lumen 1308 of control assembly 1300. Lumen 1338 may also be accessible through an opening 1339 in slide assembly 1336.

In accordance with an embodiment of the present invention, in FIG. 13, needle 1050 may extend through lumens 1308, 1338 and out manifold cap 1310 of control assembly 1300, and into a distal end of an injection actuator 1340. Specifically, needle 1050 may extend from a hub 1342, for example, but not limited to, a Luer hub, at a proximal end of injection actuator 1340, pass through a firing mechanism 1345 and pass out of a distal end of injection actuator 1340 and into manifold cap 1310 at the proximal end of control assembly 1300. A proximal end of hub 1342 may receive the therapeutic agent and may be in fluid communication with the needle 1050. A push button actuator 1346 may be attached to and through an exterior surface of injection actuator 1340 to control firing mechanism 1345, which in turn may control the extension of the distal end of needle 1050 for the delivery of the therapeutic agent to the target tissue.

In FIG. 13, in accordance with an embodiment of the present invention, firing mechanism 1345 may be axially aligned with and attached around needle 1050, and slidably disposed in injection actuator 1340. Specifically, firing mechanism 1345 may be slidably attached to a rail 1347 that may be rigidly attached to an interior wall of injection actuator 1340. Firing mechanism 1345 may move proximally and distally along rail 1347 to retract and extend, respectively, needle 1050 out of the distal end of catheter 1000. Firing mechanism 1345 may be biased toward the distal end of injection actuator 1340 by a spring 1350, which may be disposed between a proximal end of firing mechanism 1345 and an interior distal side of a proximal end of injection actuator 1340. Firing mechanism 1345 may include a plunger 1348 that may be disposed in firing mechanism 1345 and may extend away from firing mechanism 1345 in a plane axially aligned with and substantially perpendicular to a central axis of firing mechanism 1345. When firing mechanism 1345 is moved proximally, plunger 1348 may extend away from firing mechanism 1345 and releasably engage an opening in push button actuator 1346 to hold piston 1345 in a locked, ready to be fired, position within firing mechanism body 1347. Plunger 1348 may be biased, for example, by a spring mechanism, to extend perpendicularly out and away from the central axis of plunger 1348 to engage the opening in push button actuator 1346 when plunger 1348 has moved to a predetermined position within injection actuator 1340.

In FIG. 13, in accordance with an embodiment of the present invention, push button actuator 1346 may be used to fire needle 1050 by pushing down on plunger 1348, which may release plunger 1348 from the opening in push button actuator 1346. For example, push button actuator 1346 may be hinged at a distal end to injection actuator 1340 so that when push button actuator 1346 is pressed, the proximal end of push button actuator 1346 moves inwardly toward the proximal end of firing mechanism 1345 to permit plunger 1348 to slide out of the opening in push button actuator 1346. Pushing plunger 1348 back through the opening in push button actuator 1346 may release firing mechanism 1345 to be moved distally by spring 1350. Consequently, the distal end of needle 1050 may extend past the distal end of catheter and into the target tissue that sensor 1005 may be in contact with. Hub 1342 may move distally with firing mechanism 1345 and hub 1342 may be manually pulled away from the proximal end of injection actuator 1340 to re-lock firing mechanism 1345 in push button actuator 1346 with plunger 1348.

In FIG. 13, in accordance with an embodiment of the present invention, although not its main function, hub 1342 may limit the firing distance of spring 1350 when a distal end of hub 1342 strikes the proximal end of injection actuator 1340. Hub 1342, in general, is at a predetermined fixed distance from the proximal end of injection actuator 1340 and thus may not contact the proximal end of injection actuator 1340 if, for example, the injection depth controlled by send marker band 1052 on needle 1050 is less than the predetermined fixed distance hub 1342 is from the proximal end of injection actuator 1340.

Figure 14:
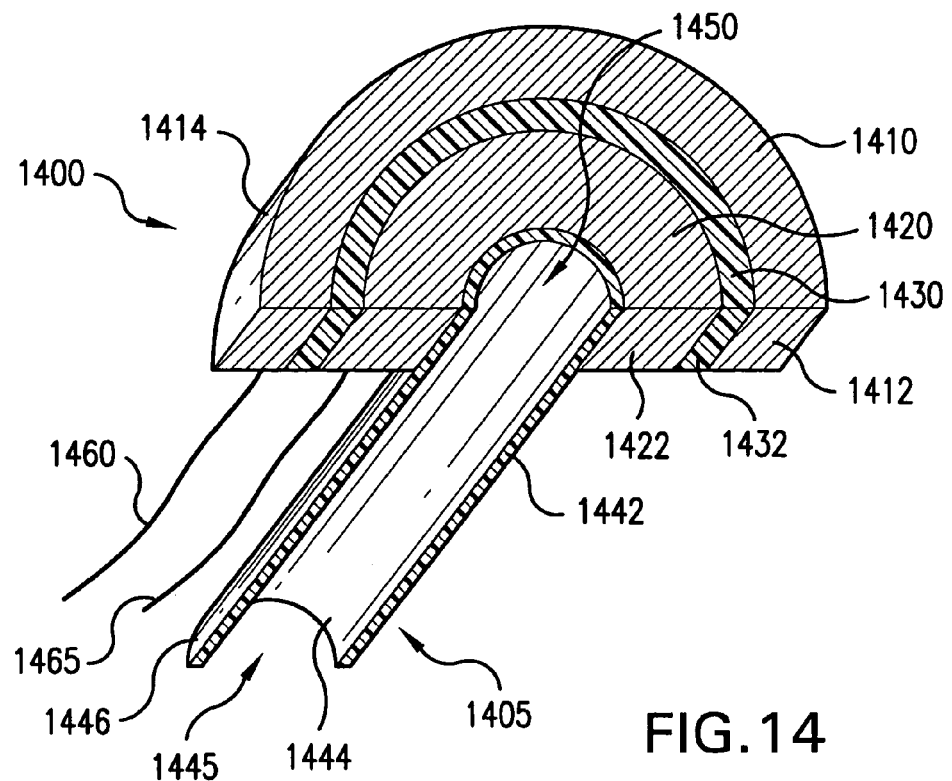
FIG. 14 is a cross-sectional perspective view of the distal end of a dual ring sensor, in accordance with an embodiment of the present invention.

FIG. 14 is a cross-sectional perspective view of the distal end of a dual ring sensor, in accordance with an embodiment of the present invention. In FIG. 14, a sensor 1400 on a catheter 1405 may include a first electrode 1410 and a second electrode 1420 with an insulator 1430 between them to form a generally circular disk shape that may be affixed directly to a distal end of catheter 1405. In the embodiment in FIG. 14, first electrode 1410 may include proximal and distal surfaces with an outer surface 1414 extending between outer edges of the proximal and distal surfaces to form a larger outer electrode that may define an axially aligned opening within which insulator 1430 and second electrode 1420 may be co-axially positioned. Electrodes 1410, 1420 may be made of any electrically conductive material, for example, # 304 stainless steel or like conductive, surgical material and may be of sufficient thickness to prevent deformation of sensor 1400 when it contacts a tissue site. Sensor 1400 may have a smooth, a rough and/or a slightly adhesive surface on its distal end. Specifically, first electrode 1410, second electrode 1420 and insulator 1430 may each have the same or any combination of different surfaces based on the requirements of the specific use for which sensor 1400 may be used. The rough and slightly adhesive surfaces may help prevent sensor 1400 from moving and/or jumping off the tissue site, for example, when a needle is deployed out of the catheter. In an alternate embodiment, sensor 1400 may have small protrusions on its distal end that may penetrate or merely depress tissue when placed against the tissue to also help prevent sensor 1400 from moving and/or jumping off the tissue site when the needle is deployed out of the catheter. Each of the moving and/or jumping prevention embodiments may be particularly useful in locations that may experience significant movement of the tissue, for example, an AV node in the heart.

In FIG. 14, insulator 1430 may include any non-conductive material or adhesive, for example, a urethane adhesive, having, but not limited to, a thickness of approximately 0.020 or more inches between electrodes 1410, 1420. For example, in addition to greater thickness, for example, 0.030 and 0.040 inches, insulator 1430 may be of a thickness of less than 0.020 inches depending on the propensity of first electrode 1410 and second electrode 1420 to short circuit each other. Insulator 1430 may also include TEFLON™ or a non-conductive plastic. Second electrode 1410 may have an axially aligned opening 1440 extending from its proximal surface to its distal surface in which catheter 1405 may be co-axially coupled to second electrode 1410. Catheter 1405 may include a substantially cylindrical wall 1442 having a distal end and a proximal end with an inner surface 1444 running there between to define a lumen 1445. Catheter 1405 may also include an outer surface 1446 running from the proximal end to the distal end of catheter 1405. Inner surface 1444 at the distal end of catheter 1405 may define an opening 1450. Opening 1450 may be of sufficient diameter to permit the extension and retraction of a needle (not shown for ease of illustration) through sensor 1400 without contacting the needle against either first electrode 1410 or second electrode 1420. In accordance with embodiments of the present invention, sensor 1400 may be manufactured and the sizing of opening 1450 may be set by inserting a non-stick insulator 1430, for example, TEFLON™, between first electrode 1410 and second electrode 1420 and sliding the two electrodes and insulator 1430 onto a non-stick catheter 1405, for example, a TEFLON™ tube, having lumen 1445 with a predetermined internal diameter. Wicking and/or injecting the adhesive into the gap between electrodes 1410, 1420 may insert an adhesive, for example, an insulating adhesive. When the adhesive has set, sensor 1400 may be removed from the non-stick tube, the non-stick core may be removed from opening 1440, and any excess adhesive may be trimmed from sensor 1400. Alternatively, first electrode 1410 and second electrode 1420 may have an adhesive applied to their respective opposing side faces and the non-stick core and one or more preformed insulating pieces may be assembled between first electrode 1410 and second electrode 1420 and then the entire assembly may be slid into the non-stick tube, or some other clamping device until the adhesive may set.

In FIG. 14, although the shape of sensor 1400 may be shown in this embodiment as being generally circular, the shape is not determinative of how sensor 1400 operates, and other embodiments are possible, for example, oval/ovoid, square and hemispherical shapes, some of which will be shown and detailed in subsequent figures and description. Insulator 1430, for example, may be used to fix the electrodes 1410, 1420 together. Likewise, other embodiments are contemplated in which sensor 1400 may be segmented into three or more electrodes that may be fixed to, but electrically insulated from, each other. Likewise, in accordance with an embodiment of the present invention, insulator 1430 may extend around the inside of opening 1440 to form an annular insulating band, which may further assure that needle 1450 does not touch either first electrode 1410 or second electrode 1420. Alternatively, a separate insulator may be used for this purpose. Similarly, in accordance with an embodiment of the present invention, sensor 1400 may be a single electrode with two or more spatially oriented lead wires attached thereto to act as a thermocouple detection device by measuring the impedance between the lead wires.

Figure 15:
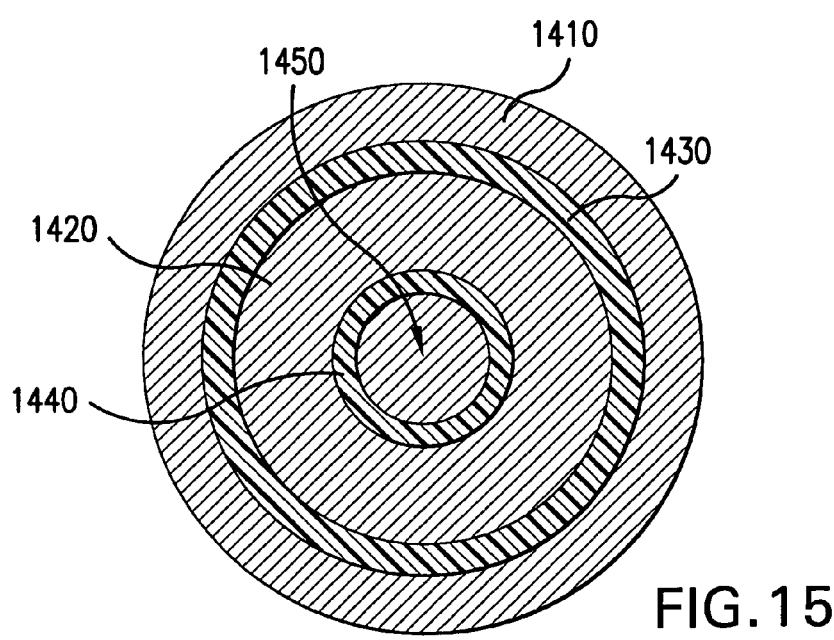
FIG. 15 is a front-end view of the distal end of the dual ring sensor of FIG. 14, in accordance with another embodiment of the present invention.

FIG. 15 is a front-end view of the distal end of the dual ring sensor of FIG. 14, in accordance with an embodiment of the present invention. In FIG. 15, a dual ring sensor 1400 may include a first electrode 1410, a second electrode 1420 and an insulator 1430 and may be attached to a catheter 1405. First electrode 1410, second electrode 1420 and insulator 1430 may each be substantially annular and co-axially aligned with and attached to each other. For example, in accordance with the present embodiment, first electrode 1410 may be larger than insulator 1430, which may be larger than second electrode 1420. First electrode 1410 may include a first electrode distal surface 1411, a first electrode proximal surface (not shown), a first electrode outer surface 1414 and a first electrode inner surface (not shown). Similarly, second electrode 1420 may include a second electrode distal surface (not shown), a second electrode proximal surface (not shown), a second electrode outer surface (not shown) and a second electrode inner surface (not shown). Insulator 1430 may include an insulator distal surface (not shown), an insulator proximal surface (not shown), an insulator outer surface (not shown) and an insulator inner surface (not shown). Specifically, an inner surface of first electrode 1410 may encircle and be attached to an outer surface of insulator 1430 and an inner surface of insulator 1430 may encircle and be attached to an outer surface of second electrode 1420 to form sensor 1400.

In FIG. 15, the second electrode inner surface may define an opening 1450 through which catheter 1405 may be disposed and outer surface 1446 of catheter 1405 may be attached to the second electrode inner surface that defines opening 1450. Catheter 1405 may also have a distal end defining a distal opening, a proximal end defining a proximal opening, an inner surface 1444 defining a lumen 1445 extending there between.

Figure 16A:
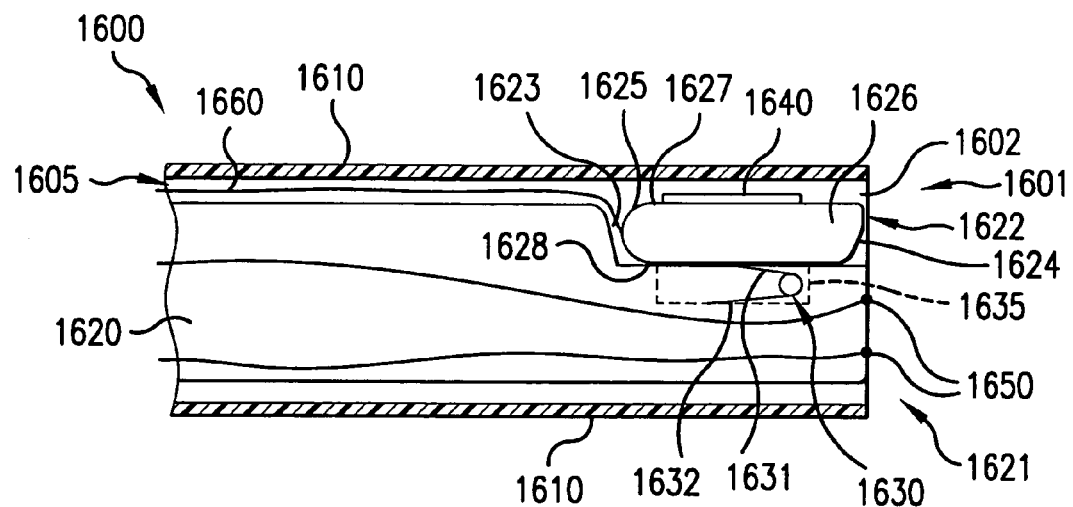
FIG. 16A is a cross-sectional side view of the distal end of a catheter with sensing electrodes and a flip-top portion to deliver a therapeutic, the catheter in a retracted position, in accordance with an embodiment of the present invention.

FIG. 16A is a partial cross-sectional side view of the distal end of a catheter with sensing electrodes and a flip-top portion to deliver a therapeutic, the catheter in a retracted position, in accordance with an embodiment of the present invention. In FIG. 16A, a catheter sensor device 1600 may include a substantially cylindrical outer sheath 1610 and a catheter 1620 recessed within outer sheath 1610. Outer sheath 1610 may include a sheath distal end 1601 defining a distal opening 1602, a sheath proximal end (not shown) defining a proximal opening (not shown), and a lumen 1605 extending there between. Catheter 1620 may include a non-conductive material, as previously described herein, having a catheter distal end 1621 with a flip top tab 1622 attached to and disposed in a notched portion 1623 of distal end 1621. Flip top tab 1622 may include a bottom edge 1624, a top edge 1625 that may be substantially parallel to bottom edge 1624 and a pair of substantially parallel to each other opposing side edges 1626 (only one is shown in FIG. 16A) perpendicular to and extending between bottom edge 1624 and top edge 1625. Flip top tab 1622 may also include a front surface 1627 perpendicular to and running between top edges of bottom edge 1624, top edge 1625 and opposing side edges 1626; and a back surface 1628 that is substantially parallel to front surface 1627 and perpendicular to and running between bottom edges of bottom edge 1624, top edge 1625 and opposing side edges 1626.

In FIG. 16A, in accordance with the present embodiment, flip top tab 1622 may be attached to catheter distal end 1621, for example, by means of a hinge 1630, which may have a first hinge portion 1631 attached to back surface 1628 of flip top tab 1622 and moveably attached to a second hinge portion 1632 that may be attached to a recess 1635 in catheter distal end 1621. In the present embodiment, hinge 1630 may be completely recessed within recess 1635 when flip top tab 1622 is not deployed and lying flat against and parallel to catheter 1620 in notched portion 1623. Embodiments of the present invention are contemplated in which, for example, hinge 1630 may be biased toward either a recessed (closed, non-deployed, etc.) position within recess 1635, biased toward a non-recessed (open, deployed, etc.) position where flip top tab 1622 may be in a substantially perpendicular alignment with catheter 1620, and/or unbiased. In the biased embodiments, hinge 1630 may be biased, for example, by incorporating an appropriate biasing mechanism, such as a spring and/or a tension member, into hinge 1630. Front surface 1627 may have disposed thereon a therapeutic 1640 to be positioned against a target tissue. Therapeutic 1640 may include a solid, a gel, a paste, and/or any viscous solution therapeutic that would stay attached to and in the same position on front surface 1627 during transport of catheter sensor device 1600 to the target tissue.

In FIG. 16A, in accordance with the present embodiment, catheter 1620 may also include multiple sensors 1650, for example, electrodes, with which to locate a desired target tissue site. Each multiple sensor 1650 may be separate and electrically insulated from all of the other multiple sensors 1650. For example, in the present embodiment, two sensors 1650 may be disposed within catheter 1620 and be in electrical communication with the proximal end of catheter 1620. Two sensors 1650 may be used to detect electrical signals, or more accurately potential differences between the different areas of tissue that they contact. Specifically, distal end 1621 may be positioned against a potential target tissue site, either while still within outer sheath 1610, partially extended, or sufficiently extended past sheath distal end 1601 to permit the deployment of flip top tab 1622. In general, flip top tab 1622 may not be deployed until two sensors 1650 locate the desired target tissue site to prevent the loss of therapeutic 1640 due to its incorrect placement at an undesirable tissue site.

In FIG. 16A, catheter sensor device 1600 may also include an actuator control wire 1660 extending through lumen 1605 from the proximal end of catheter sensor device 1600 and attached to top edge 1625 of flip top tab 1622. Actuator control wire 1660 may be a rigid, semi-rigid or soft wire and may be controlled from the proximal end of catheter sensor device 1600. In embodiments with a rigid and/or semi-rigid actuator control wire 1660 it may be used to both deploy and retract flip top tab 1622 and each may be used with or without hinge 1630 being biased. In embodiments with a soft actuator control wire 1660 it may be used to both deploy and retract flip top tab 1622 and may be used with or without hinge 1630 being biased. However, if actuator wire 1660 is soft and hinge 1630 is unbiased, an additional means and/or method for deploying flip top tab 1622 may be needed.

Figure 16B:
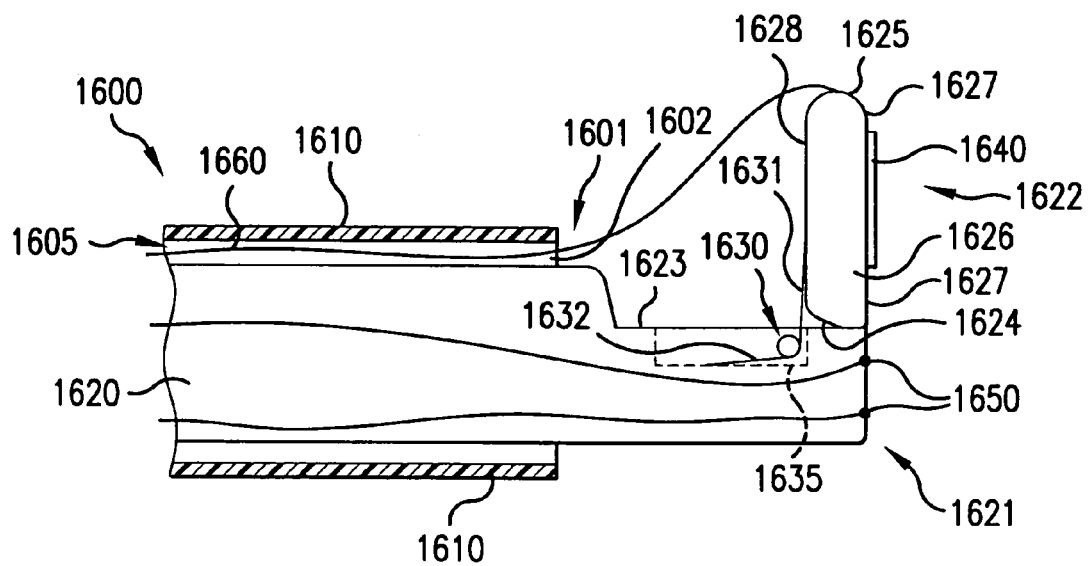
FIG. 16B is a cross-sectional side view of the distal end of the catheter of FIG. 16A in an extended position with the flip-top portion also extended, in accordance with an embodiment of the present invention.

FIG. 16B is a partial cross-sectional side view of the distal end of the catheter of FIG. 16A in an extended position and with the flip-top portion also extended, in accordance with an embodiment of the present invention. In FIG. 16B, a portion of catheter distal end 1621 is shown extended beyond sheath distal end 1601 with flip top tab 1622 in its extended (deployed) position. In this position, flip top tab 1622 may be substantially perpendicular to catheter 1620 to present therapeutic 1640 on front surface 1627 for application to the target tissue site. In FIG. 16B, hinge 1630 may be in an open position to permit second hinge portion 1632 to be extended out of recess 1635 to support flip top tab 1622. Flip top tab 1622 may be deployed using actuator control wire 1660 from the proximal end of catheter sensor device 1600 by urging actuator control wire 1660 to move distally. In general, deploying of flip top tab 1622 may include physically urging flip top tab 1622 to the fully deployed position shown in FIG. 16B and releasing a locking mechanism (not shown) that may restrain a hinge biased flip top tab 1622 from moving to the deployed position. Conversely, flip top tab 1622 may be retracted using actuator control wire 1660 from the proximal end of catheter sensor device 1600 by urging actuator control wire 1660 to move proximally and pull flip top tab 1622 back to the retracted position of FIG. 16A.

Figure 17A:
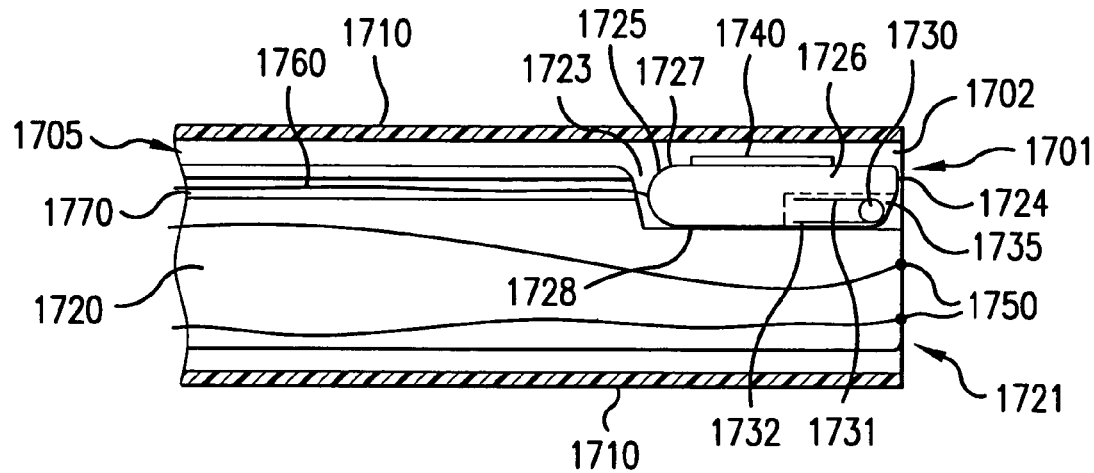
FIG. 17A is a cross-sectional side view of the distal end of a catheter with sensing electrodes and a flip-top portion to deliver a therapeutic, the catheter in a retracted position, in accordance with another embodiment of the present invention.

FIG. 17A is a cross-sectional side view of the distal end of a catheter with sensing electrodes and a flip-top portion to deliver a therapeutic of FIG. 16A, the catheter in a retracted position, in accordance with another embodiment of the present invention. In FIG. 17A, the present embodiment, while similar to that of FIG. 16A, provides an alternative embodiment in which the hinge and recess of FIG. 16A may be contained within the flip top tab and the actuator control wire may be feed through a lumen within the catheter. Specifically, In FIG. 17A, a catheter sensor device 1700 may include a substantially cylindrical outer sheath 1710 and a catheter 1720 recessed within outer sheath 1710. Outer sheath 1710 may include a sheath distal end 1701 defining a distal opening 1702, a sheath proximal end (not shown) defining a proximal opening (not shown), and a lumen 1705 extending there between. Catheter 1720 may include a non-conductive material, as previously described herein, having a catheter distal end 1721 with a flip top tab 1722 attached to and disposed in a notched portion 1723 of distal end 1721. Flip top tab 1722 may include a bottom edge 1724, a top edge 1725 that may be substantially parallel to bottom edge 1724 and a pair of substantially parallel to each other opposing side edges 1726 (only one is shown in FIG. 17A) perpendicular to and extending between bottom edge 1724 and top edge 1725. Flip top tab 1722 may also include a front surface 1727 perpendicular to and running between top edges of bottom edge 1724, top edge 1725 and opposing side edges 1726; and a back surface 1728 that is substantially parallel to front surface 1727 and perpendicular to and running between bottom edges of bottom edge 1724, top edge 1725 and opposing side edges 1726.

In FIG. 17A, in accordance with the present embodiment, flip top tab 1722 may be attached to catheter distal end 1721, for example, by means of a hinge 1730, which may have a first hinge portion 1731 attached to a recess 1735 in flip top tab 1722 and moveably attached to a second hinge portion 1732 that may be attached to a notched portion 1723. In the present embodiment, hinge 1730 may be completely recessed within recess 1735 when flip top tab 1722 is not deployed and lying flat against and parallel to catheter 1720 in notched portion 1723. Embodiments of the present invention are contemplated in which, for example, hinge 1730 may be biased toward either a recessed (closed, non-deployed, etc.) position within recess 1735, biased toward a non-recessed (open, deployed, etc.) position where flip top tab 1722 may be in a substantially perpendicular alignment with catheter 1720, and/or unbiased. In the biased embodiments, hinge 1730 may be biased, for example, by incorporating an appropriate biasing mechanism, such as a spring and/or a tension member, into hinge 1730. Front surface 1727 may have disposed thereon a therapeutic 1740 to be positioned against a target tissue. Therapeutic 1740 may include a solid, a gel, a paste, and/or any viscous solution therapeutic that would stay attached to and in the same position on front surface 1727 during transport of catheter sensor device 1700 to the target tissue.

In FIG. 17A, in accordance with the present embodiment, catheter 1720 may also include multiple sensors 1750, for example, electrodes, with which to locate a desired target tissue site. Each multiple sensor 1750 may be separate and electrically insulated from all of the other multiple sensors 1750. For example, in the present embodiment, two sensors 1750 may be disposed within catheter 1720 and be in electrical communication with the proximal end of catheter 1720. Two sensors 1750 may be used to detect electrical signals, or more accurately potential differences between the different areas of tissue that they contact. Specifically, distal end 1721 may be positioned against a potential target tissue site, either while still within outer sheath 1710, partially extended, or sufficiently extended past sheath distal end 1701 to permit the deployment of flip top tab 1722. In general, flip top tab 1722 may not be deployed until two sensors 1750 locate the desired target tissue site to prevent the loss of therapeutic 1740 due to its incorrect placement at an undesirable tissue site.

In FIG. 17A, catheter sensor device 1700 may also include an actuator control wire 1760 extending through a lumen 1770 in catheter 1720 from the proximal end of catheter sensor device 1700 and attached to top edge 1725 of flip top tab 1722. Actuator control wire 1760 may be a rigid, semi-rigid or soft wire and may be controlled from the proximal end of catheter sensor device 1700. In embodiments with a rigid and/or semi-rigid actuator control wire 1760 it may be used to both deploy and retract flip top tab 1722 and each may be used with or without hinge 1630 being biased. In embodiments with a soft actuator control wire 1760 it may be used to both deploy and retract flip top tab 1722 and may be used with or without hinge 1730 being biased. However, if actuator wire 1760 is soft and hinge 1730 is unbiased, an additional means and/or method for deploying flip top tab 1722 may be needed.

Figure 17B:
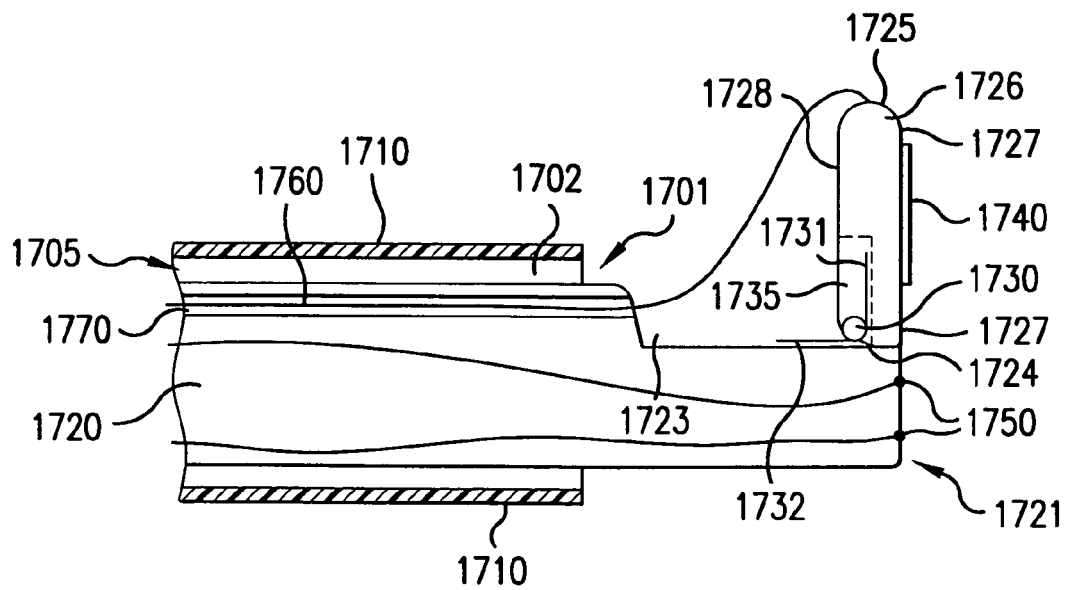
FIG. 17B is a cross-sectional side view of the distal end of the catheter of FIG. 17A in an extended position with the flip-top portion also extended, in accordance with the other embodiment of the present invention.

FIG. 17B is a cross-sectional side view of the distal end of the catheter of FIG. 17A in an extended position with the flip-top portion also extended, in accordance with the other embodiment of the present invention. In FIG. 17B, a portion of catheter distal end 1721 is shown extended beyond sheath distal end 1701 with flip top tab 1722 in its extended (deployed) position. In this position, flip top tab 17622 may be substantially perpendicular to catheter 1720 to present therapeutic 1740 on front surface 1727 for application to the target tissue site. In FIG. 17B, hinge 1730 may be in an open position to permit second hinge portion 1732 to be extended out of recess 1735 to support flip top tab 1722. Flip top tab 1722 may be deployed using actuator control wire 1760 from the proximal end of catheter sensor device 1700 by urging actuator control wire 1760 to move distally. In general, deploying of flip top tab 1722 may include physically urging flip top tab 1722 to the fully deployed position shown in FIG. 17B and releasing a locking mechanism (not shown) that may restrain a hinge biased flip top tab 1722 from moving to the deployed position. Conversely, flip top tab 1722 may be retracted using actuator control wire 1760 from the proximal end of catheter sensor device 1700 by urging actuator control wire 1760 to move proximally and pull flip top tab 1722 back to the retracted position of FIG. 17A.

FIG. 18 is a cross-sectional side view of the distal end of a catheter with sensing electrodes and an expandable component to deliver a therapeutic, the expandable component in an unexpanded position, in accordance with an embodiment of the present invention. In FIG. 18, a catheter sensor device 1800 may include a substantially cylindrical outer sheath 1810 and a catheter 1820 recessed within outer sheath 1810. Outer sheath 1810 may include a sheath distal end 1801 defining a distal opening 1802, a sheath proximal end (not shown) defining a proximal opening (not shown), and a lumen 1805 extending there between. Catheter 1820 may include a substantially cylindrical wall 1821, which may be made of a non-conductive material, as previously described herein, having a proximal end (not shown) and a distal end 1822. Substantially cylindrical wall 1821 of catheter 1820 may define a catheter lumen 1825 extending between the proximal end and distal end 1822 of catheter 1820.

In FIG. 18, distal end 1822 of catheter 1820 may be coupled to and sealably surrounded by an expandable component 1830 with an inner lumen 1831. Substantially cylindrical wall 1821 may also define one or more openings 1824 near distal end 1822 that may be enclosed by expandable component 1830 and put inner lumen 1831 in fluid communication with catheter lumen 1825. Expandable component 1830 may include a distal surface 1832 that may be in substantially planar alignment with distal end 1822 and distal surface 1832 may include an expandable porous or permeable material to permit the passage therethrough of fluids, for example, therapeutics from inner lumen 1831. Expandable component 1830 may also include a side wall 1834 depending proximally from an outer edge of distal surface 1832 to attach to substantially cylindrical wall 1821 proximal of one or more openings 1824. Substantially cylindrical wall 1821 may include an expandable non-porous/impermeable material. Expandable component 1830 may be expanded by the introduction of a fluid under a positive pressure into inner lumen 1831 from catheter lumen 1825. Conversely, expandable component 1830 may be contracted by withdrawing the fluid from inner lumen 1831 under a negative pressure. In general, the overall shape of expandable component 1830 does not have an impact on the effectiveness of expandable component 1830. However, the orientation of distal surface 1832 may significantly impact the effectiveness. Specifically, the flatter and larger the area distal surface 1832 can present to the target tissue site the more effective expandable component 1830 will be in distributing the fluid. In general, the shape of distal surface 1832 does not have a significant impact on the effectiveness of expandable component 1830. However, the closer distal surface 1832 is to the size and shape of the target tissue the more efficiently the fluid may be applied to the target tissue, which may minimize any negative impacts the fluid may have on surrounding tissue.

In FIG. 18, in accordance with the present embodiment, catheter 1820 may also include multiple sensors 1850, for example, electrodes, with which to locate a desired target tissue site. Each multiple sensor 1850 may be separate and electrically insulated from all of the other multiple sensors 1850. For example, in the present embodiment, two sensors 1850 may be disposed within catheter 1820 and be in electrical communication with the proximal end of catheter 1820. Two sensors 1850 may be used to detect electrical signals, or more accurately potential differences between the different areas of tissue that they contact. Specifically, distal end 1822 may be positioned against a potential target tissue site, either while still within outer sheath 1810, partially extended, or sufficiently extended past sheath distal end 1801 to permit the expansion of expandable component 1830. In general, expandable component 1830 may not be deployed until two sensors 1850 locate the desired target tissue site to prevent the loss of therapeutic 1840 due to its incorrect placement at an undesirable tissue site.

FIG. 19 is a cross-sectional side view of the distal end of a catheter with sensing electrodes and an expandable component to deliver a therapeutic, the expandable component in an expanded position, in accordance with an embodiment of the present invention. In FIG. 19, in accordance with the present embodiment, distal end 1822 of catheter 1820 and expandable component 1830 may be extended past sheath distal end 1801 to permit the expansion of expandable component 1830 through the introduction of fluid into inner lumen 1831. In general, the fluid, for example, a therapeutic, may escape from expandable component 1830 through porous/permeable distal surface 1832 at the tissue site.

FIG. 20 is a front-end view of the distal end of the catheter of FIG. 19 with the expandable component in the expanded position, in accordance with an embodiment of the present invention. In FIG. 20, porous/permeable distal surface 1832 may be seen in its expanded configuration around distal end 1822 of catheter 1820. Expanding porous/permeable distal surface 1832 may not only increase the rate at which a fluid within expandable component lumen 1831 can escape through distal surface 1832, but also enable the fluid to begin escaping. For example, in its contracted state, the pores of distal surface 1832 may be closed and not permit the fluid to escape.

FIG. 21 is a front-end view of an alternative dual sensor configuration for the distal end of the catheter of FIG. 19, in accordance with another embodiment of the present invention. In FIG. 21, distal end 1822 may include an outer sensor 2110, and inner sensor 2120 and an insulating ring 2130 and may be constructed similar to sensor 1400 in FIG. 14. In FIG. 21I, outer sensor 2110 may be a substantially annular ring configuration surrounding insulating ring 2130, which, may also be of a substantially annular ring configuration. Insulating ring 2130 may surround inner sensor 2120, which may be of a substantially circular configuration. As in FIGS. 18 and 19, in FIG. 21, although not shown, outer sensor 2110 and inner sensor 2120 may be in electrical communication with the proximal end of catheter 1820.

Figure 22:
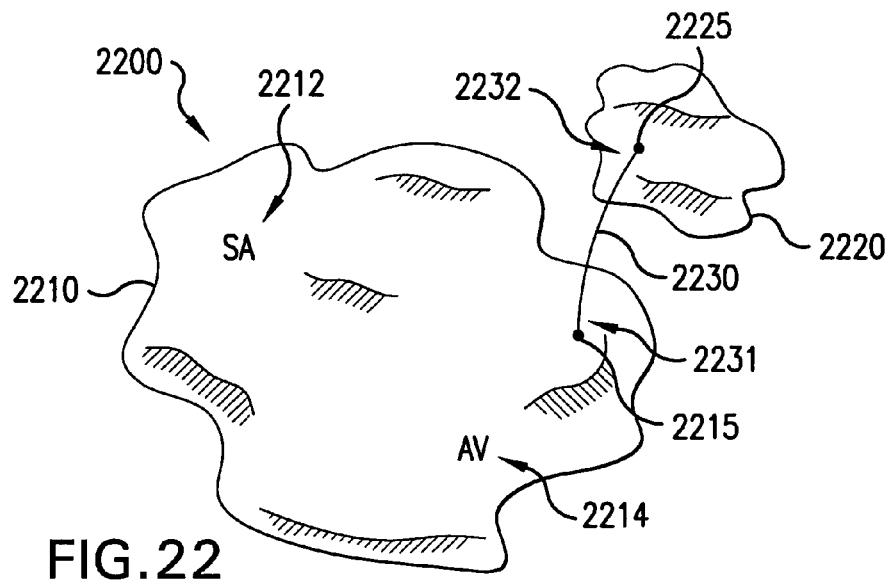
FIG. 22 is a top view of a first tissue section surrounding a sinoatrial ("SA") node and an atrioventricular ("AV") node and a second tissue section located away from but electrically connected to the first tissue section by a wire, in accordance with an embodiment of the present invention.

FIG. 22 is a top view of a first tissue section surrounding a sinoatrial ("SA") node and an atrioventricular ("AV") node and a second tissue section located away from but electrically connected to the first tissue section by a wire, in accordance with an embodiment of the present invention. In FIG. 22, an area of tissue 2200, for example, heart tissue, may include a first tissue section 2210 that may include a SA node 2212 and an AV node 2214. Area of tissue 2200 may also include a second tissue section 2220 that may be physically separated from first tissue section 2210 so as to be electrically insulated from first tissue section 2210. First tissue section 2210 may be electrically coupled to second tissue section 2220 by a wire 2230 having a proximal end 2231 and a distal end 2232 with an anchoring means at each end. The anchoring means may include, for example, a multiple wing tip, embodiments of which will be described in subsequent paragraphs. Proximal end 2231 of wire 2230 may be attached to a first point 2215 in first tissue section 2210 and distal end 2232 of wire 2230 may be attached to a second point 2225 in second tissue section 2220. Wire 2230 may include any biologically inert (i.e., bio-compatible) and electrically conductive material, for example, gold, etc., and be of a sufficient gauge (for example, 18 to 24 gauge) to prevent breaking. Wire 2330 may also be of a length greater than a distance between first point 2215 and second point 2225, for example, 1" to 1½". The length of wire 2230 may be longer than the distance to permit natural tissue movement to occur without pulling wire 2230 out of one or both of first point 2215 and second point 2225. Selecting the material used for wire 2230 based on its conductance may permit a level of control of the signal strength that may be passed across wire 2230, for example, gold has a much higher conductance level that does stainless steel.

Figure 23:
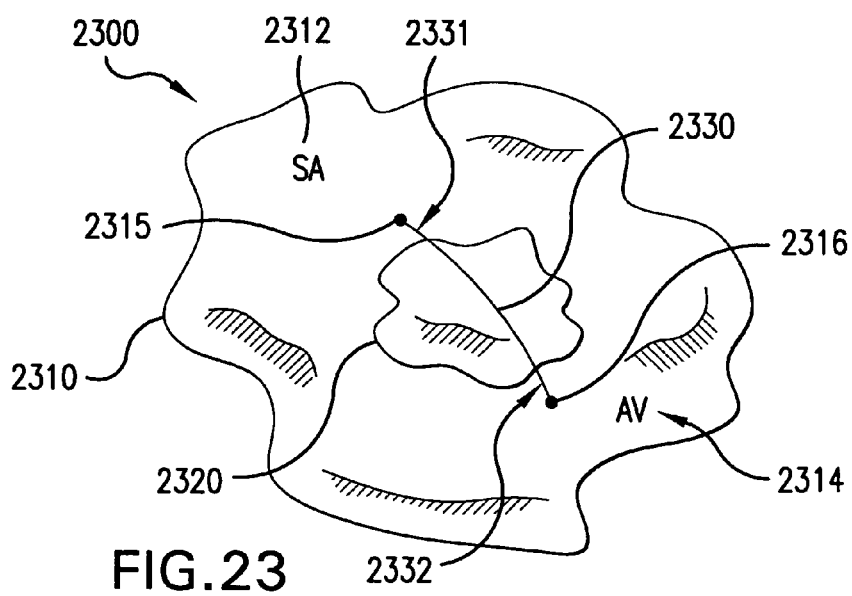
FIG. 23 is a top view of a tissue section surrounding a sinoatrial ("SA") node and an atrioventricular ("AV") node with a damaged interior tissue section located between the SA and AV nodes having a wire embedded in the tissue section to electrically connect the SA and AV nodes, in accordance with an embodiment of the present invention.

FIG. 23 is a top view of a tissue section surrounding a SA node and an AV node with a damaged interior tissue section located between the SA and AV nodes having a wire embedded in the tissue section to electrically connect the SA and AV nodes, in accordance with an embodiment of the present invention. In FIG. 23, an area of tissue 2300, for example, heart tissue, may include a first tissue section 2310 that may include a SA node 2312 and an AV node 2314. Area of tissue 2300 may also include a second tissue section 2320 located between SA node 2312 and AV node 2314 and that may be physically surrounded by first tissue section 2210 so as to electrically insulated SA node 2312 from AV node 2314. SA node 2312 may be electrically coupled to AV node 2314 by a wire 2330 having a proximal end 2331 and a distal end 2332 with an anchoring means at each end. The anchoring means may include, for example, a multi-wing tip, embodiments of which will be described in subsequent paragraphs. Proximal end 2331 of wire 2330 may be embedded at a first point 2315 near SA node 2312 in first tissue section 2310 and distal end 2332 of wire 2330 may be embedded at a second point 2316 near AV node 2314 in first tissue section 2310. Wire 2330 may include any biologically inert (i.e., bio-compatible) and electrically conductive material, for example, gold, platinum, etc., and be of a sufficient gauge (for example, 24 to 26 gauge) and strength to prevent breaking. In general, wire 2330 may be selected to be of a length greater than a distance between first point 2315 and second point 2316, for example, 1" to 1½". The length of wire 2330 may be longer than the distance to permit natural tissue movement to occur without pulling wire 2330 out of one or both of first point 2315 and second point 2316. Selecting a material and/or a composition of material that is to be used for wire 2330 based on its conductance may permit a level of control of the signal strength that may be passed across wire 2330. For example, since gold has a much higher conductance level that stainless steel, gold would conduct more of an original signal from the first point to the second point than would the stainless steel.

Figure 24:
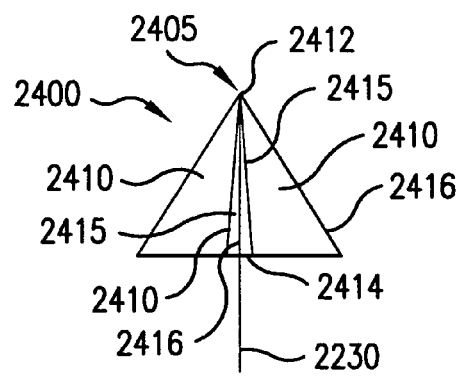
FIG. 24 is a side view of a four-wing tip anchor configuration of the wire in FIGS. 22 and 23, in accordance with an embodiment of the present invention.

FIG. 24 is a side view of a four-wing tip anchor configuration of the wire in FIGS. 22 and 23, in accordance with an embodiment of the present invention. In FIG. 24, an anchor 2400 may include multiple wings 2410, for example, four, that may be evenly distributed around wire 2230, 2330 of FIGS. 22 and 23. In FIG. 24, each wing 2410 may include a distal end 2412 and a proximal end 2414. Distal end 2412 of each wing 2410 may taper to a point with a thin cross-section and may be coupled to each other distal end 2412 to form a tip 2405 of anchor 2400. Wing 2410 may have opposing, substantially triangularly-shaped side walls 2415 that proximally extend and angle away from distal end 2412 to proximal end 2414 so that proximal end 2414 may form a substantially flat surface. Outer edges of opposing, substantially triangularly-shaped side walls 2415 may meet to form a sharp edge 2416 that may be used to slice into tissue to install anchor 2400. The flat surface of proximal end 2414 may prevent anchor 2400 from being withdrawn from the tissue in which it is embedded, since it acts as a blunt stop against the tissue in which it is embedded.

FIG. 25 is a top view of an alternative three-wing tip anchor configuration of the wire in FIGS. 22 and 23 loaded in a wire deployment tool with the three-wing tips in a folded position and ready for insertion into a target tissue site, in accordance with an embodiment of the present invention. In FIG. 25, a wire deployment tool 2500 may include an outer wall 2510 which may define a lumen 2505 in which may be disposed a push catheter 2520 with a catheter lumen 2525. Catheter lumen 2525 may have disposed therein a wire 2530 with three wing tips 2540 attached at a distal end of wire 2530. In FIG. 25, three wing tips 2540 may be folded to fit within lumen 2505 of outer wall 2510 to permit wire 2530 to pass through lumen 2505 of outer wall 2510. Although not shown, a proximal end of wire 2530 may have the same three wing tips 2540 attached thereto. Other embodiments are contemplated in which two, four or more wing tips may be attached to the distal and proximal ends of wire 2530.

In general, in accordance with some embodiments of the present invention, in FIG. 25 and subsequent figures related to a wire deployment tool, the wire deployment tool may use a multi-lumen design. For example, in FIG. 25, a three-lumen design, with proximal and distal ends may include an outer wall defining an outer wall lumen, a first push rod/catheter with a first push/rod lumen disposed in the outer wall lumen, and a second push rod/catheter either with or without a second push rod/catheter lumen disposed in the first push rod/catheter lumen. Each outer wall and push rod/catheter and their respective lumens may extend from the proximal to the distal end of the wire deployment tool and each end of the wall and push rods/catheters may define an opening to permit access to their respective lumens. Each push rod/catheter may be controllable from their respective proximal ends. This design permits the outer wall to prevent the sharp anchors from contacting and damaging vessel walls during navigation of the wire deployment tool to a desired target tissue site. In addition, the first push rod/catheter may be used to deploy a first multi-wing anchor and an end of the wire into the target tissue site and the second push rod/catheter may be used to deploy a second multi-wing anchor and an other end of the wire into the target tissue site. Each multi-wing anchor, i.e., tip, may include foldable wings that may be folded to fit within one of the lumens in the wire deployment tool. This enables the wings to expand past a diameter of the wire deployment tool, which aids in securing each multi-wing anchor in the target tissue site. Other embodiments are also contemplated in which the multi-wing anchors may have fixed wings, although this may result in less wing area, which may reduce the anchoring ability of each multi-wing anchor.

FIG. 26 is a cross-sectional side view of a distal end of the three-wing tip anchor and wire deployment tool of FIG. 25 showing the wing tips in their folded position within the wire deployment tool, in accordance with an embodiment of the present invention. In FIG. 26, outer wall 2510 of wire deployment tool 2500 may have a distal end 2601 that defines an opening into lumen 2505 in which the distal end of wire 2530 with a three-wing anchor 2602 attached thereto may be positioned. In FIG. 26, each wing 2540 of three-wing anchor 2602 may include may include a distal end 2612 and a proximal end 2614. Distal end 2612 of each wing 2540 may taper to a point with a thin cross-section and may be coupled to every other distal end 2612 to form a tip 2605 of three-wing anchor 2602. Wing 2540 may have opposing, substantially triangularly-shaped side walls 2615 that proximally extend and angle away from distal end 2612 to proximal end 2614 so that proximal end 2614 may form a substantially flat surface. Outer edges of opposing, substantially triangularly-shaped side walls 2615 may meet to form a sharp edge 2616 that may be used to slice into tissue to install three-wing anchor 2602. The flat surface of proximal end 2614 may prevent three-wing anchor 2602 from being withdrawn from the tissue in which it is embedded, since it acts as a blunt stop against the tissue in which it is embedded. A distal end 2521 of push catheter 2520 may be positioned against the flat surface of proximal end 2614 of three-wing anchor 2602 to push the distal end of wire 2530 and three-wing anchor 2602 out of lumen 2505 and past distal end 2601 of outer wall 2510 of wire deployment tool 2500.

FIG. 27 is a cross-sectional side view of the distal end of the three-wing tip anchor and wire deployment tool of FIGS. 25 and 26 showing the tip in an unfolded position outside the wire deployment tool, in accordance with an embodiment of the present invention.

FIG. 28 is a cross-sectional side view of a distal portion the wire deployment tool of FIG. 25 showing a wire with a first tip and a second tip in their folded positions within the distal end of the wire deployment tool, in accordance with an embodiment of the present invention. In FIG. 28, a wire deployment tool 2800 may include an outer wall 2810 with a distal end 2801 that defines an opening into a lumen 2805 in which a wire 2830 with a distal end 2831 having a first multi-wing anchor 2802 attached thereto may be positioned. Lumen 2505 may have disposed therein a push catheter 2820 having a substantially flat distal end 2821 that may define an opening to a push catheter lumen 2825 within which wire 2830 may extend proximally to a second multi-wing anchor 2803 attached at a proximal end 2832 of wire 2830.

In FIG. 28, each wing 2840 of first multi-wing anchor 2802 and second multi-wing anchor 2803 may include a distal end 2612 and a proximal end 2614. A distal end 2812 of each wing 2840 may taper to a point with a thin cross-section and may be coupled to every other distal end 2812 to form a tip 2806 of multi-wing anchor 2802. Wing 2840 may have opposing, substantially triangularly-shaped side walls 2815 that proximally extend and angle away from distal end 2812 to proximal end 2814 so that proximal end 2814 may form a substantially flat surface. Outer edges of opposing, substantially triangularly-shaped side walls 2815 may meet to form a sharp edge 2816 that may be used to slice into tissue to install multi-wing anchor 2802. The flat surface of proximal end 2814 may prevent multi-wing anchor 2802 from being withdrawn from the tissue in which it is embedded, since it acts as a blunt stop against the tissue in which it is embedded. As seen in FIG. 28, second multi-wing anchor 2803 may be oriented so that tip 2806 is pointed in the same direction as tip 2806 of first multi-wing anchor 2802. As a result, wire 2830 may be curved into a U-shaped position at proximal end 2832 to permit second multi-wire anchor 2803 to be oriented as illustrated.

In FIG. 28, substantially flat distal end 2821 may be positioned against the flat surface of proximal end 2614 of first multi-wing anchor 2802 to push the distal end of wire 2830 and multi-wing anchor 2802 out of lumen 2805 and past distal end 2801 of outer wall 2810 of wire deployment tool 2800. Push catheter 2825 may also have disposed therein a push rod 2850 with a substantially flat distal end 2851 that may be positioned against the flat surface of proximal end 2614 of second multi-wing anchor 2803 to push the proximal end of wire 2830 and three-wing anchor 2802 out of lumen 2805 and past distal end 2801 of outer wall 2810 of wire deployment tool 2800. Distal end 2851 of push rod 2850 may have a concave groove 2853 defined therein to accept and hold fast wire 2830 at the U-shaped portion at proximal end 2832. Push rod 2850 may have a lock mechanism associated with concave groove 2853 to hold the U-shaped portion of proximal end 2832 until it is deemed appropriate to release second multi-wing anchor 2803. In general, for example, a simple latch (not shown) that may be controlled by a push/pull wire (not shown) from the proximal end of wire deployment tool 2800 may be implemented as the lock mechanism. In embodiments of the present invention, wire deployment tool 2800 may be used with any of the catheters with sensing electrodes described herein to facilitate the correct and accurate placement of wire 2830. In addition, embodiments of wire deployment tool 2800 may be used with any catheter system that may permit delivery of wire 2830 to a desired target tissue site.

FIG. 29 is a cross-sectional side view of the wire and the wire deployment tool of FIG. 28 showing the first tip in an unfolded position extending past the distal end of the wire deployment tool, in accordance with an embodiment of the present invention. In FIG. 29, first multi-wing anchor 2802 may be seen in its unfolded position extending past distal end 2801 of wire deployment tool 2800 and push catheter 2820 may be seen to be retracted away from first multi-wing anchor 2802 and back into lumen 2805. Although not shown for ease of illustration, first multi-wing anchor 2802 may be embedded in a first target tissue site, for example, first point 2215 of FIG. 22, and, in FIG. 29, wire deployment tool 2800 may be moved to a second target tissue site so that second multi-wing anchor 2803 may be embedded in a second target tissue site.

FIG. 30 is a cross-sectional side view of the wire and the wire deployment tool of FIGS. 28 and 29 showing both the first and second tips in unfolded positions extending past the distal end of the wire deployment tool, in accordance with an embodiment of the present invention. In FIG. 29, push rod 2850 may be urged distally to eject second multi-wing anchor 2803 past distal end 2801 of wire deployment tool 2800 to be embedded into the second target tissue site. As seen in FIG. 29, wings 2840 of second multi-wing anchor 2803 have unfolded and, although not shown for ease of illustration, second multi-wing anchor 2803 may be embedded in the second target tissue site, for example, second point 2225 of FIG. 22. In FIG. 30, push rod 2850 may release U-shaped portion of wire 2830 and be moved proximally to be retracted past distal end 2801 of wire deployment tool 2800 back into lumen 2805 of outer wall 2810 and push catheter lumen 2825.

Figure 31:
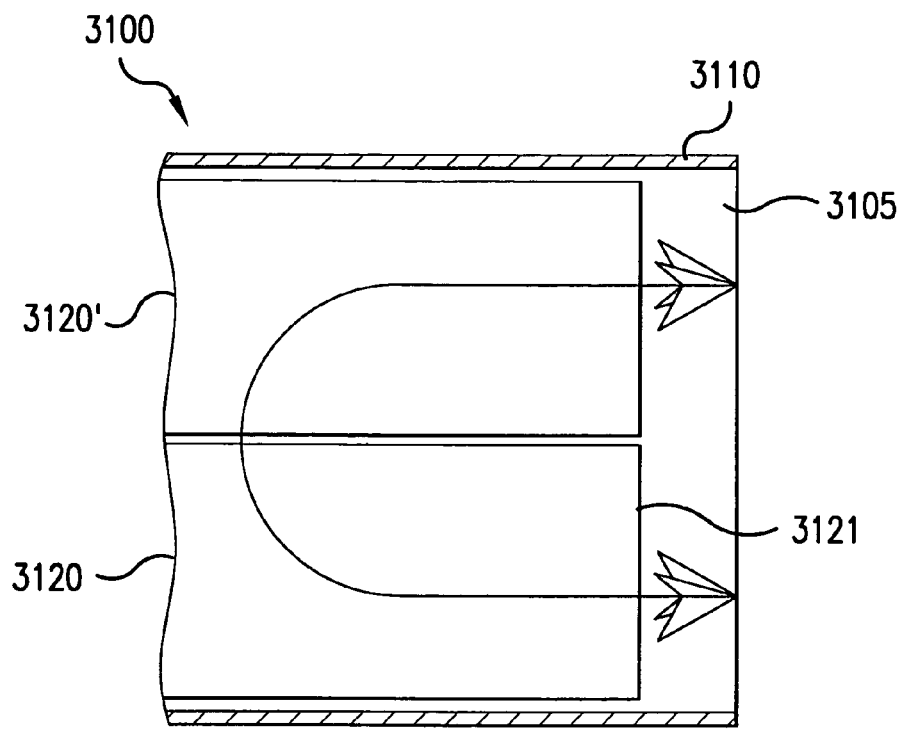
FIG. 31 is a cross-sectional side view of a wire with wire tips in an alternative wire deployment tool, in accordance with an embodiment of the present invention.

FIG. 31 is a cross-sectional side view of a wire with wire tips in an alternative wire deployment tool, in accordance with an embodiment of the present invention. In FIG. 31, a wire deployment tool 3100 may include an outer wall 3110 that may define a lumen 3105 in which two substantially parallel and separately controllable push rods, a first push rod 3120 and a second push rod 3120' may be disposed. Although each push rod 3120, 3120' may be identically configured, for ease of illustration only first push rod 3120 will be described herein. However, is to be clearly understood that the following description of first push rod 3120 is equally applicable to second push rod 3120'. First push rod 3120 may include a distal end 3121 and a proximal end (not shown) located at and controllable from the proximal end of wire deployment tool 3100. Distal end 3121 may include a gripping portion to hold a portion of a wire 3130 near a first multi-wing anchor 3140 located at an end of wire 3130. The push rods 3120 and 3120' may then be urged forward to thrust anchor 3140 into target tissue. Once lodged in the tissue, the push rod may be retracted, leaving the anchor 3140 secured to the target tissue.

Figure 32:
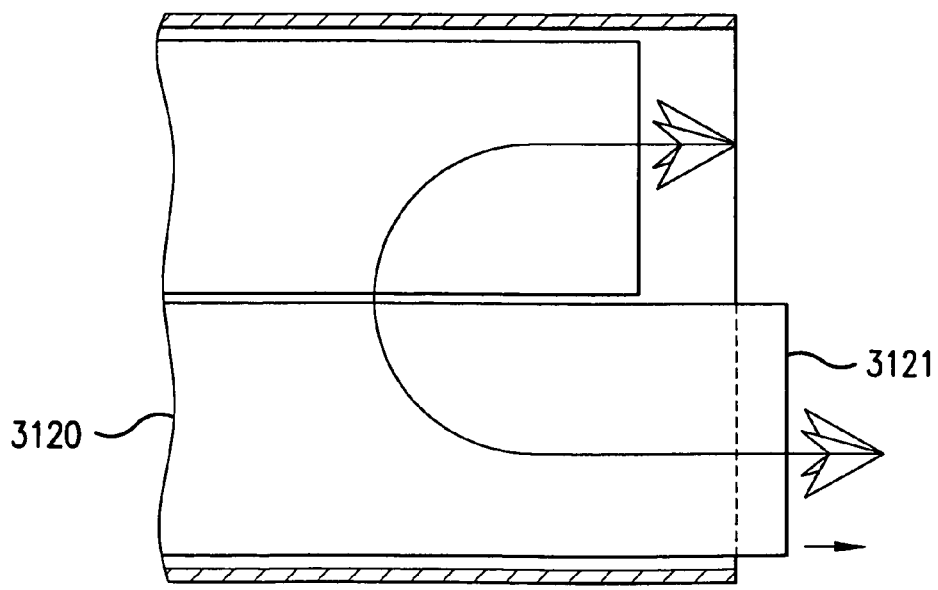
FIG. 32 is a cross-sectional side view of the wire with one of the wire tips extending past a distal end of the alternative wire deployment tool of FIG. 31, in accordance with an embodiment of the present invention.

FIG. 32 is a cross-sectional side view of the wire with one of the wire tips extending past a distal end of the alternative wire deployment tool of FIG. 31, in accordance with an embodiment of the present invention. As can be seen, the push rod 3120 has been urged forward in this embodiment as would be done to secure anchor 3140 to a target area.

A detailed description of embodiments of catheter assemblies that may be used in embodiments of the present invention may be found in co-pending U.S. patent application Ser. No. 09/635,083, filed by the same assignee on Aug. 8, 2000 and entitled "Catheter Shaft Assembly," which is hereby incorporated by reference in its entirety.

The therapeutic agent may be any pharmaceutically acceptable agent such as a non-genetic therapeutic agent, a biomolecule, a small molecule, or cells.

Exemplary non-genetic therapeutic agents include anti-thrombogenic agents such heparin, heparin derivatives, prostaglandin (including micellar prostaglandin E1), urokinase, and PPack (dextrophenylalanine proline arginine chloromethylketone); anti-proliferative agents such as enoxaprin, angiopeptin, sirolimus (rapamycin), tacrolimus, everolimus, monoclonal antibodies capable of blocking smooth muscle cell proliferation, hirudin, and acetylsalicylic acid; anti-inflammatory agents such as dexamethasone, rosiglitazone, prednisolone, corticosterone, budesonide, estrogen, estradiol, sulfasalazine, acetylsalicylic acid, mycophenolic acid, and mesalamine; anti-neoplastic/anti-proliferative/anti-mitotic agents such as paclitaxel, epothilone, cladribine, 5-fluorouracil, methotrexate, doxorubicin, daunorubicin, cyclosporine, cisplatin, vinbiastine, vincristine, epothulones, endostatin, trapidil, halofuginone, and angiostatin; anti-cancer agents such as antisense inhibitors of c-myc oncogene; anti-microbial agents such as triclosan, cephalosporins, aminoglycosides, nitrofurantoin, silver ions, compounds, or salts; biofilm synthesis inhibitors such as non-steroidal anti-inflammatory agents and chelating agents such as ethylenediaminetetraacetic acid, O,O'-bis (2-aminoethyl)ethyleneglycol-N,N,N',N'- tetraacetic acid and mixtures thereof; antibiotics such as gentamycin, rifampin, minocyclin, and ciprofolxacin; antibodies including chimeric antibodies and antibody fragments; anesthetic agents such as lidocaine, bupivacaine, and ropivacaine; nitric oxide; nitric oxide (NO) donors such as linsidomine, molsidomine, L-arginine, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, warfarin sodium, Dicumarol, aspirin, prostaglandin inhibitors, platelet aggregation inhibitors such as cilostazol and tick antiplatelet factors; vascular cell growth promoters such as growth factors, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogenous vascoactive mechanisms; inhibitors of heat shock proteins such as geldanamycin; and any combinations and prodrugs of the above.

Exemplary biomolecules include peptides, polypeptides and proteins; oligonucleotides; nucleic acids such as double or single stranded DNA (including naked and cDNA), RNA, antisense nucleic acids such as antisense DNA and RNA, small interfering RNA (siRNA), and ribozymes; genes; carbohydrates; angiogenic factors including growth factors; cell cycle inhibitors; and anti-restenosis agents. Nucleic acids may be incorporated into delivery systems such as, for example, vectors (including viral vectors), plasmids or liposomes.

Non-limiting examples of proteins include monocyte chemoattractant proteins ("MCP-1) and bone morphogenic proteins ("BMP's"), such as, for example, BMP-2, BMP-3, BMP-4, BMP-5, BMP-6 (Vgr-1), BMP-7 (OP-1), BMP-8, BMP-9, BMP-10, BMP-11, BMP-12, BMP -13, BMP-14, BMP-15. Preferred BMPS are any of BMP-2, BMP-3, BMP-4, BMP-5, BMP-6, and BMP-7. These BMPs can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them. Non-limiting examples of genes include survival genes that protect against cell death, such as anti-apoptotic Bcl-2 family factors and Akt kinase and combinations thereof. Non-limiting examples of angiogenic factors include acidic and basic fibroblast growth factors, vascular endothelial growth factor, epidermal growth factor, transforming growth factor a and β, platelet-derived endothelial growth factor, platelet-derived growth factor, tumor necrosis factor α, hepatocyte growth factor, and insulin like growth factor. A non-limiting example of a cell cycle inhibitor is a cathespin D(CD) inhibitor. Non-limiting examples of anti-restenosis agents include p15, p16, p18, p19, p21, p27, p53, p57, Rb, nFkB and E2F decoys, thymidine kinase ("TK") and combinations thereof and other agents useful for interfering with cell proliferation.

Exemplary small molecules include hormones, nucleotides, amino acids, sugars, and lipids and compounds have a molecular weight of less than 100 kD.

Exemplary cells include stem cells, progenitor cells, endothelial cells, adult cardiomyocytes, and smooth muscle cells. Cells can be of human origin (autologous or allogenic) or from an animal source (xenogenic), or genetically engineered.

Any of the therapeutic agents may be combined to the extent such combination is biologically compatible.

Any of the above mentioned therapeutic agents may be incorporated into a polymeric coating on the medical device or applied onto a polymeric coating on a medical device. The polymers of the polymeric coatings may be biodegradable or non-biodegradable. Non-limiting examples of suitable non-biodegradable polymers include polyisobutylene copolymers and styrene-isobutylene-styrene block copolymers such as styrene-isobutylene-styrene tert-block copolymers (SIBS); polyvinylpyrrolidone including cross-linked polyvinylpyrrolidone; polyvinyl alcohols, copolymers of vinyl monomers such as EVA; polyvinyl ethers; polyvinyl aromatics; polyethylene oxides; polyesters including polyethylene terephthalate; polyamides; polyacrylamides; polyethers including polyether sulfone; polyalkylenes including polypropylene, polyethylene and high molecular weight polyethylene; polyurethanes; polycarbonates, silicones; siloxane polymers; cellulosic polymers such as cellulose acetate; polymer dispersions such as polyurethane dispersions (BAYHDROL®); squalene emulsions; and mixtures and copolymers of any of the foregoing.

Non-limiting examples of suitable biodegradable polymers include polycarboxylic acid, polyanhydrides including maleic anhydride polymers; polyorthoesters; poly-amino acids; polyethylene oxide; polyphosphazenes; polylactic acid, polyglycolic acid and copolymers and mixtures thereof such as poly(L-lactic acid) (PLLA), poly(D,L,-lactide), poly (lactic acid-co-glycolic acid), 50/50 (DL-lactide-co-glycolide); polydioxanone; polypropylene fumarate; polydepsipeptides; polycaprolactone and co-polymers and mixtures thereof such as poly(D,L-lactide-co-caprolactone) and polycaprolactone co-butylacrylate; polyhydroxybutyrate valerate and blends; polycarbonates such as tyrosine-derived polycarbonates and arylates, polyiminocarbonates, and polydimethyltrimethylcarbonates; cyanoacrylate; calcium phosphates; polyglycosaminoglycans; macromolecules such as polysaccharides (including hyaluronic acid; cellulose, and hydroxypropylmethyl cellulose; gelatin; starches; dextrans; alginates and derivatives thereof), proteins and polypeptides; and mixtures and copolymers of any of the foregoing. The biodegradable polymer may also be a surface erodable polymer such as polyhydroxybutyrate and its copolymers, polycaprolactone, polyanhydrides (both crystalline and amorphous), maleic anhydride copolymers, and zinc-calcium phosphate.

In a preferred embodiment, the polymer is polyacrylic acid available as HYDROPLUS® (Boston Scientific Corporation, Natick, Mass.), and described in U.S. Pat. No. 5,091,205, the disclosure of which is incorporated by reference herein. In a more preferred embodiment, the polymer is a co-polymer of polylactic acid and polycaprolactone.

Such coatings used with the present invention may be formed by any method known to one in the art. For example, an initial polymer/solvent mixture can be formed and then the therapeutic agent added to the polymer/solvent mixture. Alternatively, the polymer, solvent, and therapeutic agent can be added simultaneously to form the mixture. The polymer/solvent mixture may be a dispersion, suspension or a solution. The therapeutic agent may also be mixed with the polymer in the absence of a solvent. The therapeutic agent may be dissolved in the polymer/solvent mixture or in the polymer to be in a true solution with the mixture or polymer, dispersed into fine or micronized particles in the mixture or polymer, suspended in the mixture or polymer based on its solubility profile, or combined with micelle-forming compounds such as surfactants or adsorbed onto small carrier particles to create a suspension in the mixture or polymer. The coating may comprise multiple polymers and/or multiple therapeutic agents.

The coating can be applied to the medical device by any known method in the art including dipping, spraying, rolling, brushing, electrostatic plating or spinning, vapor deposition, air spraying including atomized spray coating, and spray coating using an ultrasonic nozzle.

The coating is typically from about 1 to about 50 microns thick. In the case of balloon catheters, the thickness is preferably from about 1 to about 10 microns, and more preferably from about 2 to about 5 microns. Very thin polymer coatings, such as about 0.2-0.3 microns and much thicker coatings, such as more than 10 microns, are also possible. It is also within the scope of the present invention to apply multiple layers of polymer coatings onto the medical device. Such multiple layers may contain the same or different therapeutic agents and/or the same or different polymers. Methods of choosing the type, thickness and other properties of the polymer and/or therapeutic agent to create different release kinetics are well known to one in the art.

The medical device may also contain a radio-opacifying agent within its structure to facilitate viewing the medical device during insertion and at any point while the device is implanted. Non-limiting examples of radio-opacifying agents are bismuth subcarbonate, bismuth oxychloride, bismuth trioxide, barium sulfate, tungsten, and mixtures thereof.

Non-limiting examples of medical devices according to the present invention include catheters, guide wires, balloons, filters (e.g., vena cava filters), stents, stent grafts, vascular grafts, intraluminal paving systems, implants and other devices used in connection with drug-loaded polymer coatings. Such medical devices may be implanted or otherwise utilized in body lumina and organs such as the coronary vasculature, esophagus, trachea, colon, biliary tract, urinary tract, prostate, brain, lung, liver, heart, skeletal muscle, kidney, bladder, intestines, stomach, pancreas, ovary, cartilage, eye, bone, and the like.

Although the present invention has been disclosed in detail, it should be understood that various changes, substitutions, and alterations may be made herein, the present invention is intended to cover various modifications and equivalent arrangements. Other examples are readily ascertainable from the above description by one skilled in the art and may be made without departing from the spirit and scope of the present invention as defined by the following claims.

What is claimed is:

1. A method for directing electrical signals within a tissue site, the method comprising:
   implanting a first end of a bio-compatible, conducting wire in a tissue site near a source of an electrical signal, comprising the steps of:
      locating the source of the electrical signal in the first tissue site with a sensor equipped catheter system; and
      implanting the first end of the bio-compatible, conducting wire near the source of the electrical signal from the sensor equipped catheter system; and
   implanting a second end of the bio-compatible, conducting wire in the tissue site near a destination location for the electrical signal.

2. The method of claim 1, wherein the implanting the first end of the bio-compatible, conducting wire in the tissue site near a source of the electrical signal comprises:
   implanting the first end of the bio-compatible, conducting wire in the tissue site near a sinoatrial node.

3. The method of claim 1, wherein the implanting the second end of the bio-compatible, conducting wire in the tissue site near the destination for the electrical signal comprises:
   implanting the second end of the bio-compatible, conducting wire in the tissue site near an atrioventricular node.

4. The method of claim 3, wherein the implanting the second end of the bio-compatible, conducting wire in the tissue site near the atriventricular node comprises:
   implanting the second end of the bio-compatible, conducting wire in the tissue site near the atrioventricular node across a non-conductive region of the tissue site.

5. The method of claim 1, wherein the implanting the second end of the bio-compatible, conducting wire in the tissue site near the destination location for the electrical signal comprises:
   locating the destination location in the tissue site with the sensor equipped catheter system; and
   implanting the second end of the bio-compatible, conducting wire near the destination location in the tissue site from the sensor equipped catheter system.

6. The method of claim 1, wherein the bio-compatible, conducting wire comprises a gold wire.

7. The method of claim 1, wherein the bio-compatible, conducting wire is a part of a medical device, the medical device comprising:

the bio-compatible, conducting metal wire having a first end and a second end, and a multi-wing tip to be implanted in a tissue site at each end.

8. The method of claim 7, wherein the bio-compatible, conducting metal wire comprises:

a gold wire.

9. The method of claim 7, wherein the bio-compatible, conducting metal wire comprises:

a gold wire having a length in the range of 1 inch to 1 ½ inches.

10. The method of claim 7, wherein each multi-wing tip comprises:

at least three foldable bio-compatible, conducting metal wings attached to the wire end to form a pointed tip for penetrating tissue at a distal end of the multi-wing tip and each wing having a substantially flat proximal end to prevent the tip from backing out of the tissue site when the tip is embedded in the tissue site.

11. The method of claim 1, wherein the bio-compatible, conducting wire is a part of a medical device, and wherein the medical device is implanted by a tool, the tool comprising:

an outer catheter with a distal end and a proximal end and an outer catheter lumen extending therebetween;

a first push rod with a distal end and a proximal end and a first push rod lumen extending therebetween, the first push rod being slidably disposed in the outer catheter lumen, and the distal end of the first push rod being adapted to engage a proximal end of a first multi-wing tip of the medical device to move the first multi-wing tip toward the distal end of the outer catheter; and a second push rod with a distal end and a proximal end, the second push rod being slidably disposed in the first push rod lumen, and the distal end of the second push rod being adapted to engage a proximal end of a second multi-wing tip of the medical device to move the second multi-wing tip toward the distal end of the outer catheter.

12. The method of claim 11, wherein the second push rod further comprises:

a second push rod lumen extending between its distal and proximal ends.

13. The method of claim 12, wherein the first multi-wing tip and the second multi-wing tip comprises:

a material that is the same as the bio-compatible, conductive wire.

14. The method of claim 11, wherein the second push rod further comprises:

a retaining member as its distal end to hold a wire attached to the second multi-wing tip.

15. The method of claim 14, wherein the retaining member further comprises:

a control mechanism located at the proximal end of the second push rod to control the retaining member at the distal end to hold and release the wire attached to the second multi-wing tip.

16. The method of claim 11, wherein the medical device further comprises:

a bio-compatible, conductive wire coupled to and extending between the first multi-wing tip and the second multi-wing tip.

\* \* \* \* \*

UNITED STATES PATENT AND TRADEMARK OFFICE
CERTIFICATE OF CORRECTION

| | | |
|---|---|---|
| PATENT NO. | : 7,565,208 B2 | Page 1 of 1 |
| APPLICATION NO. | : 11/037342 | |
| DATED | : July 21, 2009 | |
| INVENTOR(S) | : Harris et al. | |

It is certified that error appears in the above-identified patent and that said Letters Patent is hereby corrected as shown below:

On the Title page,

[*] Notice:   Subject to any disclaimer, the term of this patent is extended or adjusted under 35 USC 154(b) by 717 days.

Delete the phrase "by 717 days" and insert -- by 1220 days --

Signed and Sealed this

Twenty-seventh Day of April, 2010

David J. Kappos
*Director of the United States Patent and Trademark Office*